(12) United States Patent
Moberg et al.

(10) Patent No.: US 7,811,262 B2
(45) Date of Patent: Oct. 12, 2010

(54) SYSTEMS AND METHODS ALLOWING FOR RESERVOIR FILLING AND INFUSION MEDIUM DELIVERY

(75) Inventors: Sheldon B. Moberg, Thousand Oaks, CA (US); Ian B. Hanson, Northridge, CA (US); Paul F. Bente, IV, Los Angeles, CA (US)

(73) Assignee: Medtronic Minimed, Inc., Northridge, CA (US)

( * ) Notice: Subject to any disclaimer, the term of this patent is extended or adjusted under 35 U.S.C. 154(b) by 333 days.

(21) Appl. No.: 11/602,428

(22) Filed: Nov. 20, 2006

(65) Prior Publication Data

US 2008/0051710 A1 Feb. 28, 2008

Related U.S. Application Data

(63) Continuation-in-part of application No. 11/588,875, filed on Oct. 27, 2006.

(60) Provisional application No. 60/839,821, filed on Aug. 23, 2006.

(51) Int. Cl.
*A61M 5/28* (2006.01)
(52) U.S. Cl. .......................... 604/201; 604/86
(58) Field of Classification Search ................. 604/155, 604/86, 201
See application file for complete search history.

(56) References Cited

U.S. PATENT DOCUMENTS

| 843,587 A | 2/1907 | De Pew |
| 2,957,609 A | 10/1960 | Holmes |
| 3,771,694 A | 11/1973 | Kaminski |
| 3,963,151 A | 6/1976 | North, Jr. |
| 3,999,543 A | 12/1976 | Lacey |
| 4,089,624 A | 5/1978 | Nichols et al. |
| 4,191,225 A | 3/1980 | Ogle |

(Continued)

FOREIGN PATENT DOCUMENTS

CA 2453151 1/2003

(Continued)

OTHER PUBLICATIONS

Invitation to Pay Additional Fees dated Jan. 25, 2008 for PCT/US2007/076429.

(Continued)

*Primary Examiner*—Nicholas D Lucchesi
*Assistant Examiner*—Gerald Landry, II
(74) *Attorney, Agent, or Firm*—Foley & Lardner LLP

(57) ABSTRACT

A system includes a durable portion with a durable housing and a separable disposable portion with a disposable housing that selectively engage with and disengage from each other. The disposable housing secures to a patient and may be disposed of after it has been in use for a prescribed period. Components that normally come into contact with a patient or with an infusion medium may be part of the disposable portion to allow for disposal after a prescribed use. A reservoir for holding the infusion medium may be part of the disposable portion, and may be supported by the disposable housing. The durable portion may include other components such as electronics for controlling delivery of the infusion medium from the reservoir, and a drive device including a motor and drive linkage.

25 Claims, 22 Drawing Sheets

U.S. PATENT DOCUMENTS

| | | | |
|---|---|---|---|
| 4,573,992 A | 3/1986 | Marx | |
| 4,838,857 A | 6/1989 | Strowe et al. | |
| 4,861,335 A * | 8/1989 | Reynolds | 604/88 |
| 4,932,937 A | 6/1990 | Gustavsson et al. | |
| 4,976,696 A | 12/1990 | Sanderson et al. | |
| 5,002,527 A | 3/1991 | Reller et al. | |
| 5,053,001 A | 10/1991 | Reller et al. | |
| 5,062,834 A | 11/1991 | Gross et al. | |
| 5,090,963 A | 2/1992 | Gross et al. | |
| 5,156,591 A | 10/1992 | Gross et al. | |
| 5,176,502 A | 1/1993 | Sanderson et al. | |
| 5,186,805 A | 2/1993 | Gross et al. | |
| 5,190,522 A | 3/1993 | Wojcicki et al. | |
| 5,203,506 A | 4/1993 | Gross et al. | |
| 5,232,029 A | 8/1993 | Knox et al. | |
| 5,232,449 A | 8/1993 | Stern et al. | |
| 5,242,406 A | 9/1993 | Gross et al. | |
| 5,242,408 A | 9/1993 | Jhuboo et al. | |
| 5,246,147 A | 9/1993 | Gross et al. | |
| 5,254,096 A | 10/1993 | Rondelet et al. | |
| 5,259,732 A | 11/1993 | Stern | |
| 5,261,884 A | 11/1993 | Stern et al. | |
| 5,295,966 A | 3/1994 | Stern et al. | |
| 5,295,967 A | 3/1994 | Rondelet et al. | |
| 5,356,632 A | 10/1994 | Gross et al. | |
| 5,425,706 A | 6/1995 | Gross et al. | |
| 5,527,288 A | 6/1996 | Gross et al. | |
| 5,569,191 A * | 10/1996 | Meyer | 604/82 |
| 5,704,520 A | 1/1998 | Gross | |
| 5,779,683 A | 7/1998 | Meyer | |
| 5,800,420 A | 9/1998 | Gross et al. | |
| 5,807,375 A | 9/1998 | Gross et al. | |
| 5,820,622 A | 10/1998 | Gross et al. | |
| 5,848,991 A | 12/1998 | Gross et al. | |
| 5,851,549 A | 12/1998 | Svec | |
| 5,858,001 A | 1/1999 | Tsals et al. | |
| 5,871,125 A | 2/1999 | Gross | |
| 5,951,523 A | 9/1999 | Osterlind et al. | |
| 5,957,889 A | 9/1999 | Poulsen et al. | |
| 5,976,109 A * | 11/1999 | Heruth | 604/140 |
| 5,984,894 A | 11/1999 | Poulsen et al. | |
| 5,997,501 A | 12/1999 | Gross et al. | |
| 6,003,736 A | 12/1999 | Ljunggren | |
| 6,033,377 A | 3/2000 | Rasmussen et al. | |
| 6,070,623 A | 6/2000 | Aneas | |
| 6,099,504 A | 8/2000 | Gross et al. | |
| 6,186,982 B1 | 2/2001 | Gross et al. | |
| 6,261,272 B1 | 7/2001 | Gross et al. | |
| 6,275,717 B1 | 8/2001 | Gross et al. | |
| 6,312,409 B1 | 11/2001 | Gross | |
| 6,314,317 B1 | 11/2001 | Willis | |
| 6,346,095 B1 | 2/2002 | Gross et al. | |
| 6,364,865 B1 | 4/2002 | Lavi et al. | |
| 6,394,981 B2 | 5/2002 | Heruth | |
| 6,398,031 B1 | 6/2002 | Frezza | |
| 6,406,455 B1 | 6/2002 | Willis et al. | |
| 6,423,035 B1 * | 7/2002 | Das et al. | 604/155 |
| 6,440,096 B1 | 8/2002 | Lastovich et al. | |
| 6,474,219 B2 | 11/2002 | Klitmose et al. | |
| 6,478,771 B1 | 11/2002 | Lavi et al. | |
| 6,485,461 B1 | 11/2002 | Mason et al. | |
| 6,490,483 B2 | 12/2002 | Willis | |
| 6,508,788 B2 | 1/2003 | Preuthun | |
| 6,537,251 B2 | 3/2003 | Klitmose | |
| 6,542,350 B1 | 4/2003 | Rogers | |
| 6,585,707 B2 | 7/2003 | Cabiri et al. | |
| 6,589,229 B1 | 7/2003 | Connelly et al. | |
| 6,591,876 B2 | 7/2003 | Safabash | |
| 6,595,956 B1 | 7/2003 | Gross et al. | |
| 6,607,513 B1 | 8/2003 | Down et al. | |
| 6,613,019 B2 | 9/2003 | Munk | |
| 6,616,627 B2 | 9/2003 | Willis et al. | |
| 6,635,049 B1 | 10/2003 | Robinson et al. | |
| 6,641,565 B1 | 11/2003 | Lavi et al. | |
| 6,645,181 B1 | 11/2003 | Lavi et al. | |
| 6,652,510 B2 | 11/2003 | Lord et al. | |
| 6,656,158 B2 | 12/2003 | Mahoney et al. | |
| 6,656,159 B2 | 12/2003 | Flaherty | |
| 6,669,669 B2 | 12/2003 | Flaherty et al. | |
| 6,689,100 B2 | 2/2004 | Connelly et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,723,068 B2 | 4/2004 | Lavi et al. | |
| 6,723,072 B2 | 4/2004 | Flaherty et al. | |
| 6,740,059 B2 | 5/2004 | Flaherty | |
| 6,746,438 B1 | 6/2004 | Arnissolle | |
| 6,749,587 B2 | 6/2004 | Flaherty | |
| 6,767,188 B2 | 7/2004 | Vrane et al. | |
| 6,768,425 B2 | 7/2004 | Flaherty et al. | |
| 6,786,246 B2 | 9/2004 | Ohms et al. | |
| 6,808,506 B2 | 10/2004 | Lastovich et al. | |
| 6,830,558 B2 | 12/2004 | Flaherty et al. | |
| 6,830,560 B1 | 12/2004 | Gross et al. | |
| 6,899,699 B2 | 5/2005 | Enggaard | |
| 6,936,006 B2 | 8/2005 | Sabra | |
| 6,939,324 B2 | 9/2005 | Gonnelli et al. | |
| 6,945,417 B2 * | 9/2005 | Jansen et al. | 215/249 |
| 6,948,918 B2 | 9/2005 | Hansen | |
| 6,952,604 B2 | 10/2005 | DeNuzzio et al. | |
| 6,960,184 B2 | 11/2005 | Willis et al. | |
| 6,960,192 B1 | 11/2005 | Flaherty et al. | |
| 6,997,911 B2 | 2/2006 | Klitmose | |
| 7,008,399 B2 | 3/2006 | Larsen et al. | |
| 7,018,360 B2 | 3/2006 | Flaherty et al. | |
| 7,025,226 B2 | 4/2006 | Ramey | |
| 7,027,478 B2 | 4/2006 | Ackley | |
| 7,029,455 B2 | 4/2006 | Flaherty | |
| 7,083,592 B2 | 8/2006 | Lastovich et al. | |
| 7,083,599 B2 | 8/2006 | Alchas et al. | |
| 7,115,108 B2 | 10/2006 | Wilkinson et al. | |
| 7,128,727 B2 | 10/2006 | Flaherty et al. | |
| 7,133,329 B2 | 11/2006 | Skyggebjerg et al. | |
| 7,137,964 B2 | 11/2006 | Flaherty | |
| 7,144,384 B2 | 12/2006 | Gorman et al. | |
| 7,150,409 B2 | 12/2006 | Gonnelli et al. | |
| 7,156,838 B2 | 1/2007 | Gabel et al. | |
| 7,187,969 B2 | 3/2007 | Willis | |
| 7,220,245 B2 | 5/2007 | Kriesel | |
| 7,250,037 B2 | 7/2007 | Shermer et al. | |
| 7,390,294 B2 | 6/2008 | Hassler, Jr. | |
| 2002/0040208 A1 | 4/2002 | Flaherty et al. | |
| 2002/0072733 A1 | 6/2002 | Flaherty | |
| 2002/0123740 A1 | 9/2002 | Flaherty et al. | |
| 2002/0126036 A1 | 9/2002 | Flaherty et al. | |
| 2002/0169439 A1 | 11/2002 | Flaherty | |
| 2002/0177819 A1 * | 11/2002 | Barker et al. | 604/232 |
| 2003/0009133 A1 | 1/2003 | Ramey | |
| 2003/0055380 A1 | 3/2003 | Flaherty | |
| 2003/0073952 A1 | 4/2003 | Flaherty et al. | |
| 2003/0097092 A1 | 5/2003 | Flaherty | |
| 2003/0161744 A1 * | 8/2003 | Vilks et al. | 417/415 |
| 2003/0167035 A1 | 9/2003 | Flaherty et al. | |
| 2003/0167036 A1 | 9/2003 | Flaherty | |
| 2003/0199824 A1 | 10/2003 | Mahoney et al. | |
| 2003/0199825 A1 | 10/2003 | Flaherty | |
| 2003/0229310 A1 | 12/2003 | Flaherty et al. | |
| 2004/0010207 A1 | 1/2004 | Flaherty et al. | |
| 2004/0015131 A1 | 1/2004 | Flaherty et al. | |
| 2004/0064088 A1 | 4/2004 | Gorman et al. | |
| 2004/0064096 A1 | 4/2004 | Flaherty et al. | |
| 2004/0078028 A1 | 4/2004 | Flaherty et al. | |
| 2004/0087894 A1 | 5/2004 | Flaherty | |

| | | | |
|---|---|---|---|
| 2004/0092865 | A1 | 5/2004 | Flaherty et al. |
| 2004/0116866 | A1 | 6/2004 | Gorman et al. |
| 2004/0204673 | A1 | 10/2004 | Flaherty |
| 2004/0220551 | A1 | 11/2004 | Flaherty et al. |
| 2004/0235446 | A1 | 11/2004 | Flaherty et al. |
| 2004/0260233 | A1 | 12/2004 | Garibotto et al. |
| 2005/0022274 | A1 | 1/2005 | Campbell et al. |
| 2005/0065760 | A1 | 3/2005 | Murtfeldt et al. |
| 2005/0165363 | A1 | 7/2005 | Judson et al. |
| 2006/0178641 | A1 | 8/2006 | Reynolds |
| 2006/0264835 | A1 | 11/2006 | Nielsen et al. |
| 2007/0066939 | A1 | 3/2007 | Krulevitch et al. |
| 2007/0078428 | A1* | 4/2007 | Reynolds et al. ............ 604/411 |

FOREIGN PATENT DOCUMENTS

| | | |
|---|---|---|
| EP | 0138681 A2 | 4/1985 |
| EP | 0 614 653 A2 | 9/1994 |
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| FR | 2783433 | 3/2000 |
| WO | WO 93/02723 | 2/1993 |
| WO | WO 98/17336 | 4/1998 |
| WO | WO 99/55401 | 11/1999 |
| WO | WO 01/68166 A1 | 9/2001 |
| WO | WO 01/70307 | 9/2001 |
| WO | WO 01/76684 A1 | 10/2001 |
| WO | WO 02/20073 A2 | 3/2002 |
| WO | WO 02/28454 A2 | 4/2002 |
| WO | WO 02/40083 A2 | 5/2002 |
| WO | WO 02/49509 A2 | 6/2002 |
| WO | WO 02/068015 A2 | 9/2002 |
| WO | WO 03/008021 A1 | 1/2003 |
| WO | WO 03/024504 A2 | 3/2003 |
| WO | WO 03/033051 A1 | 4/2003 |
| WO | WO 03/059372 A2 | 7/2003 |
| WO | WO 03/059372 A3 | 7/2003 |
| WO | WO 03/074121 A1 | 9/2003 |
| WO | WO 03/090509 A2 | 11/2003 |
| WO | WO 03/090819 A2 | 11/2003 |
| WO | WO 03/090838 A1 | 11/2003 |
| WO | WO 03/103758 A1 | 12/2003 |
| WO | WO 03/103763 A1 | 12/2003 |
| WO | WO 2004/006981 A2 | 1/2004 |
| WO | WO 2004/006982 A2 | 1/2004 |
| WO | WO 2004/030716 | 4/2004 |
| WO | WO 2004/030716 A2 | 4/2004 |
| WO | WO 2004/030717 | 4/2004 |
| WO | WO 2004/030717 A2 | 4/2004 |
| WO | WO 2004/060436 A2 | 7/2004 |
| WO | WO 2004/093648 A2 | 11/2004 |
| WO | WO 2004/098390 A2 | 11/2004 |
| WO | WO 2004/098454 A2 | 11/2004 |
| WO | WO 2006/015922 A1 | 2/2006 |
| WO | WO 2006/018425 A2 | 2/2006 |
| WO | WO 2006/018425 A3 | 2/2006 |
| WO | WO 2006/018447 A2 | 2/2006 |
| WO | WO 2006/018447 A3 | 2/2006 |
| WO | WO 2006/024671 A1 | 3/2006 |
| WO | WO 2006/024672 A1 | 3/2006 |
| WO | WO 2006/042811 A2 | 4/2006 |
| WO | WO 2006/042811 A3 | 4/2006 |
| WO | WO 2006/072416 A2 | 7/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/084464 A1 | 8/2006 |
| WO | WO 2006/086980 A1 | 8/2006 |
| WO | WO 2006/089547 A1 | 8/2006 |
| WO | WO 2006/089548 A1 | 8/2006 |
| WO | WO 2006/089965 A1 | 8/2006 |
| WO | WO 2006/096746 A1 | 9/2006 |
| WO | WO 2006/097453 A1 | 9/2006 |
| WO | WO 2006/104806 A2 | 10/2006 |
| WO | WO 2006/108775 A2 | 10/2006 |
| WO | WO 2006/108809 A1 | 10/2006 |
| WO | WO 2006/116997 A1 | 11/2006 |
| WO | WO 2006/120253 A2 | 11/2006 |
| WO | WO 2006/125692 A1 | 11/2006 |
| WO | WO 2007/000425 A2 | 1/2007 |
| WO | WO 2007/000426 A2 | 1/2007 |
| WO | WO 2007/000427 A1 | 1/2007 |

OTHER PUBLICATIONS

PCT Search Report dated Apr. 11, 2008 for PCT/US2007/076429.
Final Office Action dated May 28, 2009 from related U.S. Appl. No. 11/602,428.
Office Action dated Jan. 8, 2009 from related U.S. Appl. No. 11/602,173.
Office Action dated Apr. 6, 2009 from related U.S. Appl. No. 11/602,052.
Office Action dated May 13, 2009 from related U.S. Appl. No. 11/602,173.
Office Action dated Jul. 22, 2009 from related U.S. Appl. No. 11/588,875.
Office Action dated Sep. 2, 2009 from related U.S. Appl. No. 11/602,173.
Communication Pursuant to Article 94(3) dated Jan. 11, 2010 for related European application No. 07841172.
US Notice of Allowance for U.S. Appl. No. 11/602,173 dated Jan. 1, 2010.
US Office Action for U.S. Appl. No. 11/602,052 dated Oct. 26, 2009.
US Office Action for U.S. Appl. No. 11/588,875 dated Jan. 7, 2010.
US Notice of Allowance for U.S. Appl. No. 11/602,113 dated Oct. 30, 2009.
US Office Action for U.S. patent Appl. No. 11/588,875 dated Feb. 20, 2009.
US Office Action for U.S. Appl. No. 11/602,113 dated Dec. 29, 2008.
Office Action dated May 28, 2010 from U.S. Appl. No. 11/588,875.

* cited by examiner

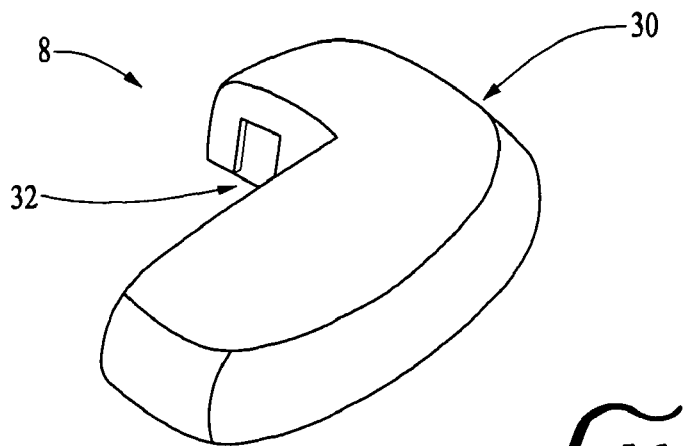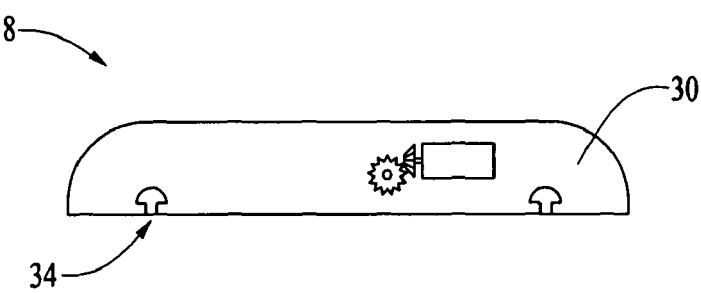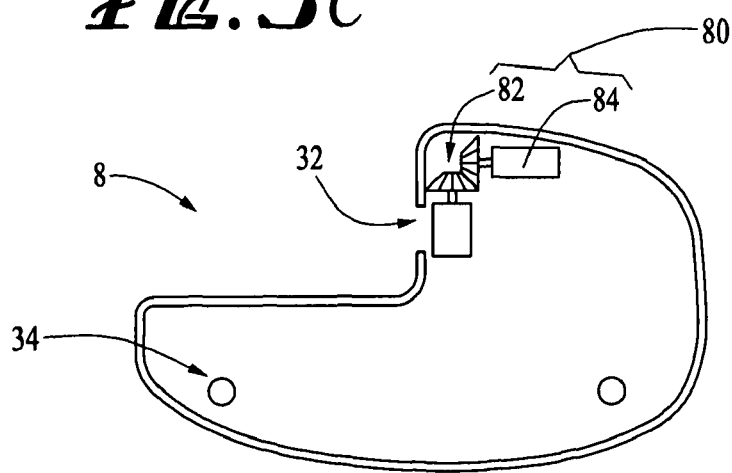

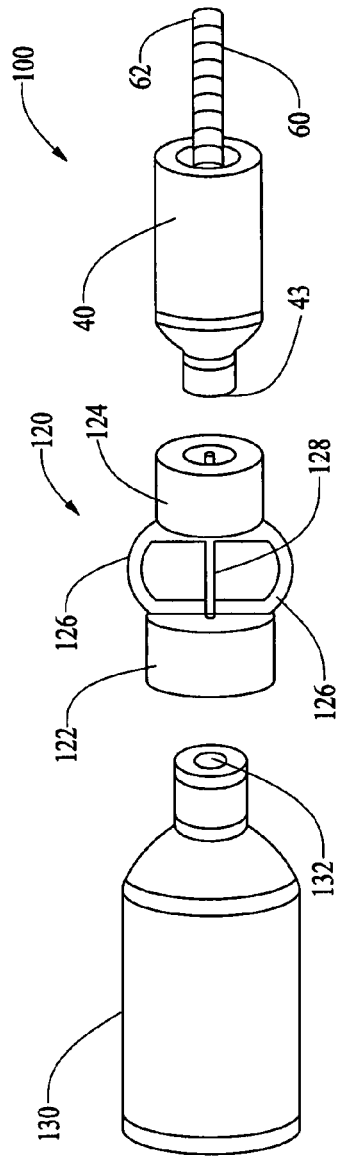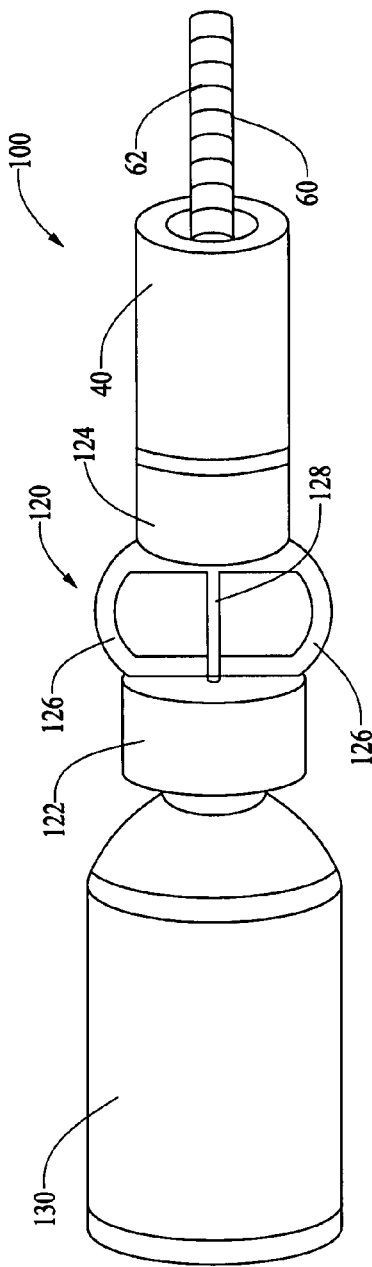

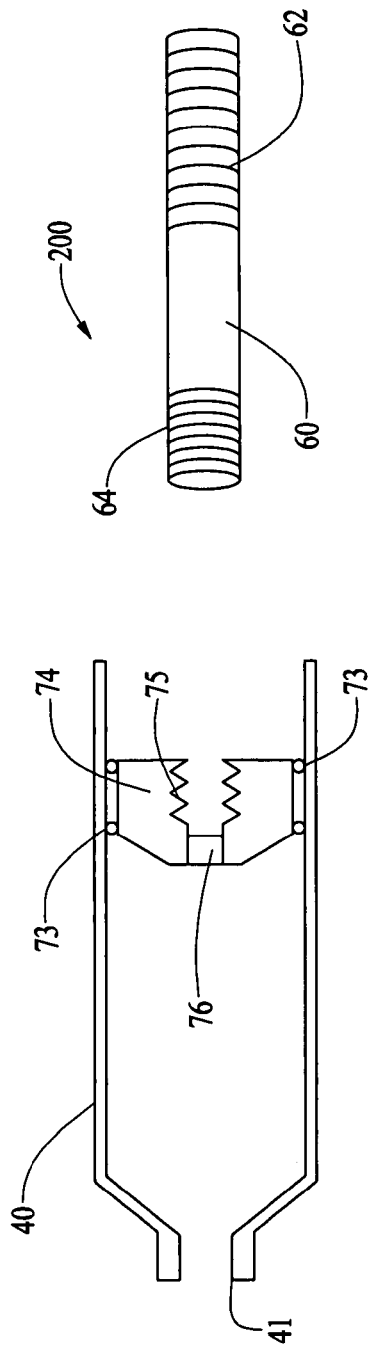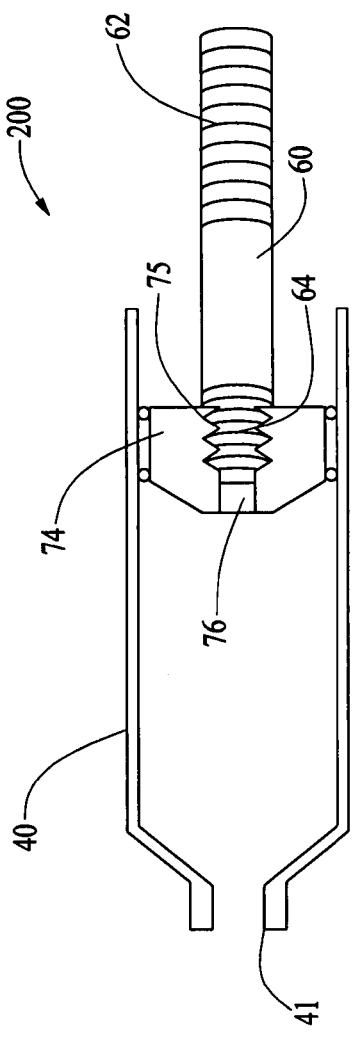

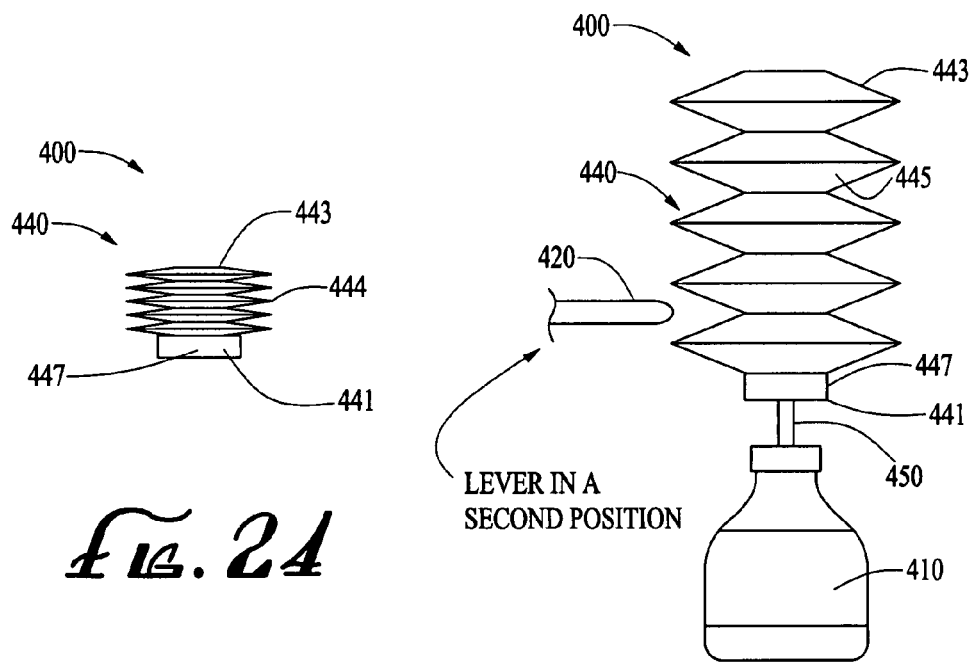
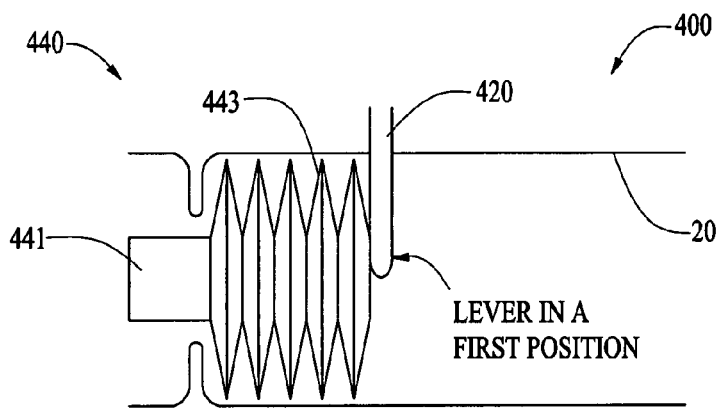

SYSTEMS AND METHODS ALLOWING FOR RESERVOIR FILLING AND INFUSION MEDIUM DELIVERY

CROSS-REFERENCE TO RELATED PATENT APPLICATIONS

This application is a continuation-in-part of U.S. patent application Ser. No. 11/588,875, filed Oct. 27, 2006, entitled "Systems and Methods Allowing for Reservoir Filling and Infusion Medium Delivery", the contents of which are incorporated by reference herein.

Embodiments of the present invention relate to U.S. Provisional Application Ser. No. 60/839,821, filed Aug. 23, 2006, entitled "Systems and Methods Allowing for Reservoir Filling and Infusion Medium Delivery", the contents of which are incorporated by reference herein and which is a basis for a claim of priority.

Embodiments of the present invention relate to U.S. Provisional Application Ser. No. 60/678,290, filed May 6, 2005, and to U.S. patent application Ser. No. 11/211,095, filed Aug. 23, 2005, each of which is incorporated by reference herein in its entirety.

Embodiments of the present invention relate to: (i) U.S. Provisional Application Ser. No. 60/839,822, filed Aug. 23, 2006, entitled "Infusion Medium Delivery Device and Method with Drive Device for Driving Plunger in Reservoir"; (ii) U.S. Provisional Application Ser. No. 60/839,832, filed Aug. 23, 2006, entitled "Infusion Medium Delivery Device and Method with Compressible or Curved Reservoir or Conduit"; (iii) U.S. Provisional Application Ser. No. 60/839,840, filed Aug. 23, 2006, entitled "Infusion Medium Delivery System, Device and Method with Needle Inserter and Needle Inserter Device and Method"; and (iv) U.S. Provisional Application Ser. No. 60/839,741, filed Aug. 23, 2006, entitled "Infusion Pumps and Methods and Delivery Devices and Methods with Same", the contents of each of which are incorporated by reference herein, in their entirety.

Embodiments of the present invention also relate to: (i) U.S. patent application Ser. No. 11/588,832, filed Oct. 27, 2006, entitled "Infusion Medium Delivery Device and Method with Drive Device for Driving Plunger in Reservoir"; (ii) U.S. patent application Ser. No. 11/588,847, filed Oct. 27, 2006, entitled "Infusion Medium Delivery Device and Method with Compressible or Curved Reservoir or Conduit"; (iii) U.S. Provisional. Patent Application Ser. No. 60/854,829, filed Oct. 27, 2006, entitled "Infusion Medium Delivery System, Device and Method with Needle Inserter and Needle Inserter Device and Method"; and (iv) U.S. patent application Ser. No. 11/589,323, filed Oct. 27, 2006, entitled "Infusion Pumps and Methods and Delivery Devices and Methods with Same", the contents of each of which are incorporated by reference herein, in their entirety.

BACKGROUND OF THE INVENTION

1. Field of the Invention

Embodiments of the present invention relate generally to structures, systems, and methods allowing for reservoir filling and, in specific embodiments, to an infusion medium delivery system allowing for filling a reservoir with an infusion medium and for delivering the infusion medium to a patient.

2. Related Art

According to modern medical techniques, certain chronic diseases may be treated by delivering a medication or other substance to the body of a patient. For example, diabetes is a chronic disease that is commonly treated by delivering defined amounts of insulin to a patient at appropriate times. Traditionally, manually operated syringes and insulin pens have been employed for delivering insulin to a patient. More recently, modern systems have been designed to include programmable pumps for delivering controlled amounts of medication to a patient. However, some programmable pump delivery systems operate for only a prescribed period of time and require disposal when one or more system components have exceeded an operational lifetime, even if other system components are still operational.

Pump type delivery devices have been configured in external devices, which connect to a patient, and have also been configured in implantable devices, which are implanted inside of the body of a patient. External pump type delivery devices include devices designed for use in a stationary location, such as a hospital, a clinic, or the like, and further include devices configured for ambulatory or portable use, such as devices that are designed to be carried by a patient, or the like. External pump type delivery devices may be connected in fluid flow communication to a patient or user, for example, through a suitable hollow tubing. The hollow tubing may be connected to a hollow needle that is designed to pierce the skin of the patient and to deliver an infusion medium therethrough. Alternatively, the hollow tubing may be connected directly to the patient as or through a cannula, or the like.

Examples of some external pump type delivery devices are described in the following references: (i) Published PCT Application WO 01/70307 (PCT/US01/09139), entitled "Exchangeable Electronic Cards for Infusion Devices"; (ii) Published PCT Application WO 04/030716 (PCT/US2003/028769), entitled "Components and Methods for Patient Infusion Device"; (iii) Published PCT Application WO 04/030717 (PCT/US2003/029019), entitled "Dispenser Components and Methods for Infusion Device"; (iv) U.S. Patent Application Pub. No. 2005/0065760, entitled "Method for Advising Patients Concerning Doses Of Insulin"; and (v) U.S. Pat. No. 6,589,229, entitled "Wearable Self-Contained Drug Infusion Device", each of which is incorporated by reference herein in its entirety.

As compared to syringes and insulin pens, pump type delivery devices can be significantly more convenient to a patient, in that accurate doses of insulin may be calculated and delivered automatically to a patient at any time during the day or night. Furthermore, when used in conjunction with glucose sensors or monitors, insulin pumps may be automatically controlled to provide appropriate doses of an infusion medium at appropriate times of need, based on sensed or monitored levels of blood glucose. As a result, pump type delivery devices have become an important aspect of modern medical treatments of various types of medical conditions, such as diabetes, and the like. As pump technologies improve and doctors and patients become more familiar with such devices, external medical infusion pump treatments are expected to increase in popularity and are expected to increase substantially in number over the next decade.

SUMMARY OF THE DISCLOSURE

Embodiments of the present invention relate to systems and methods that allow for reservoir filling. Some embodiments of the present invention allow for delivering an infusion medium from a reservoir to the body of a patient.

A system in accordance with an embodiment of the present invention includes a reservoir, a piston, a plunger shaft, and a handle. The reservoir allows for holding an infusion medium. The piston is disposed at least partially within the reservoir, and the piston is moveable to allow the infusion medium to fill into the reservoir and to force the infusion medium out of the reservoir. The plunger shaft is connected to the piston. The plunger shaft has a mating portion for mating with a linkage portion of a drive device, where the drive device allows for driving the plunger shaft so as to move the piston to force the infusion medium out of the reservoir when the linkage portion of the drive device is mated with the mating portion of the plunger shaft. The handle has a handle mating portion for mating with the mating portion of the plunger shaft. The handle is capable of being used by a user to move the plunger shaft so as to move the piston to allow the infusion medium to fill into the reservoir when the handle mating portion of the handle is mated with the mating portion of the plunger shaft.

In various embodiments, the mating portion of the plunger shaft is threaded. Also, in various embodiments, the handle mating portion of the handle is threaded. In some embodiments, the mating portion of the plunger shaft includes a partial nut, and the handle mating portion of the handle includes a threaded interface. Also, in some embodiments, the handle has a gripping arm for gripping the plunger shaft when the handle mating portion of the handle is mated with the mating portion of the plunger shaft.

In various embodiments, the reservoir has a port that is connectable to an infusion path to allow for delivering the infusion medium from the reservoir to the body of a particular user. In further embodiments, the port is connectable to a transfer path to allow for the infusion medium to be filled into the reservoir from an infusion medium container. In various embodiments, the system further includes a transfer guard that is connectable to the reservoir for providing a path to allow the infusion medium to be transferred from an infusion medium container to the reservoir.

In some embodiments, the system further includes a base adapted to be secured to a particular user, and the reservoir is connected to the base. In further embodiments, the reservoir is connectable to an infusion path to allow for delivering the infusion medium from the reservoir to the body of the particular user through an opening in the base. Also, in some embodiments, the system further includes the drive device having the linkage portion, where the drive device further includes a motor for moving the linkage portion, and where the motor is able to move the linkage portion of the drive device so as to drive the plunger shaft when the linkage portion of the drive device is mated with the mating portion of the plunger shaft.

In various embodiments, the linkage portion of the drive device is threaded. Also, in various embodiments, the system includes a disposable housing for housing the reservoir and for being secured to a particular user, and a durable housing for housing the motor of the drive device, where the durable housing is configured to be selectively engaged with and disengaged from the disposable housing. In some embodiments, the reservoir has a degassing portion that includes a hydrophobic material for allowing gases to escape from the reservoir while keeping the infusion medium within the reservoir. Also, in some embodiments, the piston has a degassing portion that includes a hydrophobic material for allowing gases to escape from the reservoir while keeping the infusion medium within the reservoir. In various embodiments, the system may include a particular degassing portion that is located anywhere in a fluid line. Also, in various embodiments, the system may include a hydrophobic material that is able to be sealed after it has been used for degassing.

A system in accordance with another embodiment of the present invention includes a reservoir and a piston. The reservoir allows for holding an infusion medium. The piston is disposed at least partially within the reservoir, and the piston is moveable within the reservoir. The piston includes a piston body and a piston septum. The piston body allows for forcing the infusion medium out of the reservoir, and the piston body is configured to have an opening. The piston septum is capable of being pierced to allow the infusion medium to be filled into the reservoir through the opening in the piston body.

In various embodiments, the piston is moveable to allow the infusion medium to be filled into the reservoir. Also, in various embodiments, the reservoir has an outlet port that is connectable to an infusion path to allow for delivering the infusion medium from the reservoir to the body of a user. In some embodiments, the piston septum is located within the opening in the piston body. Also, in some embodiments, the piston septum covers the opening in the piston body. In various embodiments, the piston septum is a self sealing septum so as to allow for keeping the infusion medium within the reservoir when the piston septum is not being pierced.

In some embodiments, the system further includes a fill apparatus. In various embodiments, the fill apparatus includes an engagement portion, a compressible portion, and a needle. In some embodiments, the engagement portion of the fill apparatus is able to engage with an engagement portion of the piston body. In various embodiments, the compressible portion is able to be compressed. Also, in various embodiments, the needle allows for piercing the piston septum when the engagement portion of the fill apparatus is engaged with the engagement portion of the piston body and the compressible portion of the fill apparatus is compressed. In some embodiments, the needle provides a path for transferring the infusion medium from an infusion medium container to the reservoir when the needle has pierced the piston septum.

In further embodiments, the fill apparatus includes a covering portion for at least partially surrounding a first end of the needle that is opposite a second end of the needle, where the second end of the needle is capable of piercing the piston septum when the engagement portion of the fill apparatus is engaged with the engagement portion of the piston body and the compressible portion of the fill apparatus is compressed. Also, in further embodiments, the piston is configured such that when the engagement portion of the fill apparatus is engaged with the engagement portion of the piston body and a user pulls on the fill apparatus, the piston moves within the reservoir so as to allow the infusion medium to be filled into the reservoir.

In some embodiments, the engagement portion of the fill apparatus is threaded, and the engagement portion of the piston body is threaded. In various embodiments, the compressible portion of the fill apparatus includes a bellows. Also, in various embodiments, the system further includes a plunger shaft having an engagement portion for engaging with the engagement portion of the piston body and having a mating portion for mating with a linkage portion of a drive device, where the drive device allowing for driving the plunger shaft so as to move the piston body to force the infusion medium out of the reservoir when the linkage portion of the drive device is mated with the mating portion of the plunger shaft.

In some embodiments, the system further includes the drive device having the linkage portion, where the drive device further includes a motor for moving the linkage portion. Also, in some embodiments, the system further includes a disposable housing for housing the reservoir and for being secured to a user, and a durable housing for housing the motor of the drive device, where the durable housing is configured to be selectively engaged with and disengaged from the disposable housing. In various embodiments, the reservoir has a degassing portion that includes a hydrophobic material for allowing gases to escape from the reservoir while keeping the infusion medium within the reservoir. Also, in various embodiments, the piston has a degassing portion that includes a hydrophobic material for allowing gases to escape from the reservoir while keeping the infusion medium within the reservoir.

A system in accordance with yet another embodiment of the present invention includes an infusion medium container, a plunger, a reservoir, and a transfer guard. The infusion medium container allows for holding an infusion medium. The plunger is disposed at least partially within the infusion medium container, and the plunger is moveable within the infusion medium container. The plunger includes a plunger body and a plunger septum. The plunger body allows for forcing the infusion medium out of the infusion medium container, and the plunger body is configured to have an opening. The plunger septum is capable of being pierced to allow the infusion medium to flow out of the infusion medium container through the opening in the plunger body. The reservoir allows for holding the infusion medium, and the reservoir has a port for receiving the infusion medium. The transfer guard has a transfer element for piercing the plunger septum and for providing a path to allow the infusion medium to be transferred from the infusion medium container to the reservoir.

In various embodiments, the infusion medium container includes a vial. Also, in various embodiments, the transfer element includes a needle. In some embodiments, the transfer guard has a first guard portion that is capable of at least partially surrounding a first end of the needle, and the transfer guard has a second guard portion that is capable of at least partially surrounding a second end of the needle. In various embodiments, the plunger septum is a self sealing septum that is able to seal after being pierced.

In some embodiments, the port of the reservoir is connectable to an infusion path to allow for delivering the infusion medium from the reservoir to the body of a user. Also, in some embodiments, the reservoir has a degassing portion that includes a hydrophobic material for allowing gases to escape from the reservoir while keeping the infusion medium within the reservoir. In various embodiments, the system further includes a piston disposed at least partially within the reservoir, where the piston is moveable to allow the infusion medium to fill into the reservoir and to force the infusion medium out of the reservoir. In further embodiments, the piston has a degassing portion that includes a hydrophobic material for allowing gases to escape from the reservoir while keeping the infusion medium within the reservoir.

In various embodiments, the system further includes a plunger shaft connected to the piston, where the plunger shaft has a mating portion for mating with a linkage portion of a drive device, and the drive device allows for driving the plunger shaft so as to move the piston to force the infusion medium out of the reservoir when the linkage portion of the drive device is mated with the mating portion of the plunger shaft. Also, in various embodiments, the system further includes the drive device having the linkage portion, where the drive device further includes a motor for moving the linkage portion. In some embodiments, the system further includes a disposable housing for housing the reservoir and for being secured to a user, and a durable housing for housing the motor of the drive device, where the durable housing is configured to be selectively engaged with and disengaged from the disposable housing.

A system in accordance with yet another embodiment of the present invention includes a reservoir. The reservoir allows for receiving an infusion medium from an infusion medium container. The reservoir includes a collapsible housing. The collapsible housing has an interior volume for holding the infusion medium. The collapsible housing is collapsible from an expanded state to reduce the interior volume and is expandable from a collapsed state to increase the interior volume. The collapsible housing is biased toward the expanded state. Also, the collapsible housing is configured such that upon the collapsible housing being expanded toward the expanded state, a pressure differential is created between the interior volume of the collapsible housing and the infusion medium container sufficient to transfer the infusion medium from the infusion medium container to the interior volume of the collapsible housing.

In various embodiments, the collapsible housing includes a bellows. In some embodiments, the collapsible housing includes a metal. Also, in some embodiments, the collapsible housing includes at least one of titanium, stainless steel, plastic, rubber, and TOPAS™. In various embodiments, the collapsible housing includes a bias member for biasing the collapsible housing toward the expanded state. In further embodiments, the bias member includes a spring.

In some embodiments, the system further includes a base adapted to be secured to a user, a durable housing portion configured to be selectively engaged with and disengaged from the base, and electronic circuitry contained in the durable housing portion. Also, in some embodiments, the reservoir is supported by the base, and the electronic circuitry is configured to control a delivery of the infusion medium from the reservoir to the body of the user when the durable housing portion and the base are engaged. In various embodiments, the system further includes a lever that is moveable among a plurality of positions including a first position and a second position, where the lever is able to keep the collapsible housing in the collapsed state when the collapsible housing is in the collapsed state and the lever is in the first position, and where the collapsible housing is able to expand to the expanded state when the lever is in the second position. In various embodiments, the lever is moveable to multiple positions along an expansion direction of the collapsible housing.

In some embodiments, the reservoir further includes a port in fluid flow communication with the interior volume of the collapsible housing, and the port is connectable to the infusion medium container. Also, in some embodiments, the system further includes a peristaltic pump for transferring the infusion medium from the collapsible housing to the body of a user. In various embodiments, the system further includes a base adapted to be secured to the user, and a durable housing portion configured to be selectively engaged with and disengaged from the base, where the reservoir is supported by the base, and where the peristaltic pump is contained in the durable housing portion.

A system in accordance with yet another embodiment of the present invention includes a reservoir. The reservoir allows for receiving an infusion medium from an infusion medium container, where the infusion medium container has an interior volume for holding the infusion medium. The reservoir includes a collapsible housing and a chamber housing. The collapsible housing has an interior volume for holding the infusion medium. The collapsible housing is collapsible from an expanded state to reduce the interior volume of the collapsible housing and is expandable from a collapsed state to increase the interior volume of the collapsible housing. The chamber housing has an interior volume bordered on at least one side by the collapsible housing such that the interior volume of the chamber housing increases as the collapsible housing collapses toward the collapsed state and such that the interior volume of the chamber housing decreases as the collapsible housing expands toward the expanded state.

In various embodiments, the collapsible housing and the chamber housing are configured such that when a gaseous pressure within the interior volume of the chamber housing is less than a particular gaseous pressure within the interior volume of the infusion medium container and the collapsible housing is in the collapsed state and a path for transferring the infusion medium is established between the interior volume of the infusion medium container and the interior volume of the collapsible housing, the collapsible housing and the chamber housing allow for a pressure differential between the interior volume of the chamber housing and the interior volume of the infusion medium container to cause the collapsible housing to expand and to cause the infusion medium to be pushed from the infusion medium container to the collapsible housing.

In some embodiments, the collapsible housing includes a bellows. Also, in some embodiments, the collapsible housing includes plastic, or the like. In various embodiments, the system further includes a base adapted to be secured to a user, a durable housing portion configured to be selectively engaged with and disengaged from the base, and electronic circuitry contained in the durable housing portion, where the reservoir is supported by the base, and where the electronic circuitry is configured to control a delivery of the infusion medium from the reservoir to the body of the user when the durable housing portion and the base are engaged.

In various embodiments, the reservoir further includes a port in fluid flow communication with the interior volume of the collapsible housing, and the port is connectable to the infusion medium container. In some embodiments, the system further includes a peristaltic pump for transferring the infusion medium from the collapsible housing to the body of a user. Also, in some embodiments, the system further includes a base adapted to be secured to the user, and a durable housing portion configured to be selectively engaged with and disengaged from the base, where the reservoir is supported by the base, and where the peristaltic pump is contained in the durable housing.

Therefore, embodiments of the present invention relate to systems that allow for reservoir filling. Such systems may allow for separating disposable components from durable components, so that the disposable components can be disposed of separate from the durable components. Various other embodiments relate to methods of making and using such systems for reservoir filling.

BRIEF DESCRIPTION OF THE DRAWINGS

FIG. 5A illustrates a durable portion of a delivery device in accordance with an embodiment of the present invention;

FIG. 5B illustrates a section view of a durable portion of a delivery device in accordance with an embodiment of the present invention;

FIG. 5C illustrates a section view of a durable portion of a delivery device in accordance with an embodiment of the present invention;

FIG. 10 illustrates another portion of an embodiment of a system in accordance with an embodiment of the present invention;

FIG. 11 illustrates a portion of an embodiment of a system in accordance with an embodiment of the present invention;

FIG. 17 illustrates another portion of an embodiment of a system in accordance with an embodiment of the present invention;

FIG. 18 illustrates the portion of an embodiment of the system in accordance with an embodiment of the present invention;

FIG. 24 illustrates an embodiment of a system in accordance with an embodiment of the present invention;

FIG. 25 illustrates an embodiment of a system in accordance with an embodiment of the present invention;

FIG. 26 illustrates an embodiment of a system in accordance with an embodiment of the present invention;

DETAILED DESCRIPTION OF PREFERRED EMBODIMENTS

Figure 1:
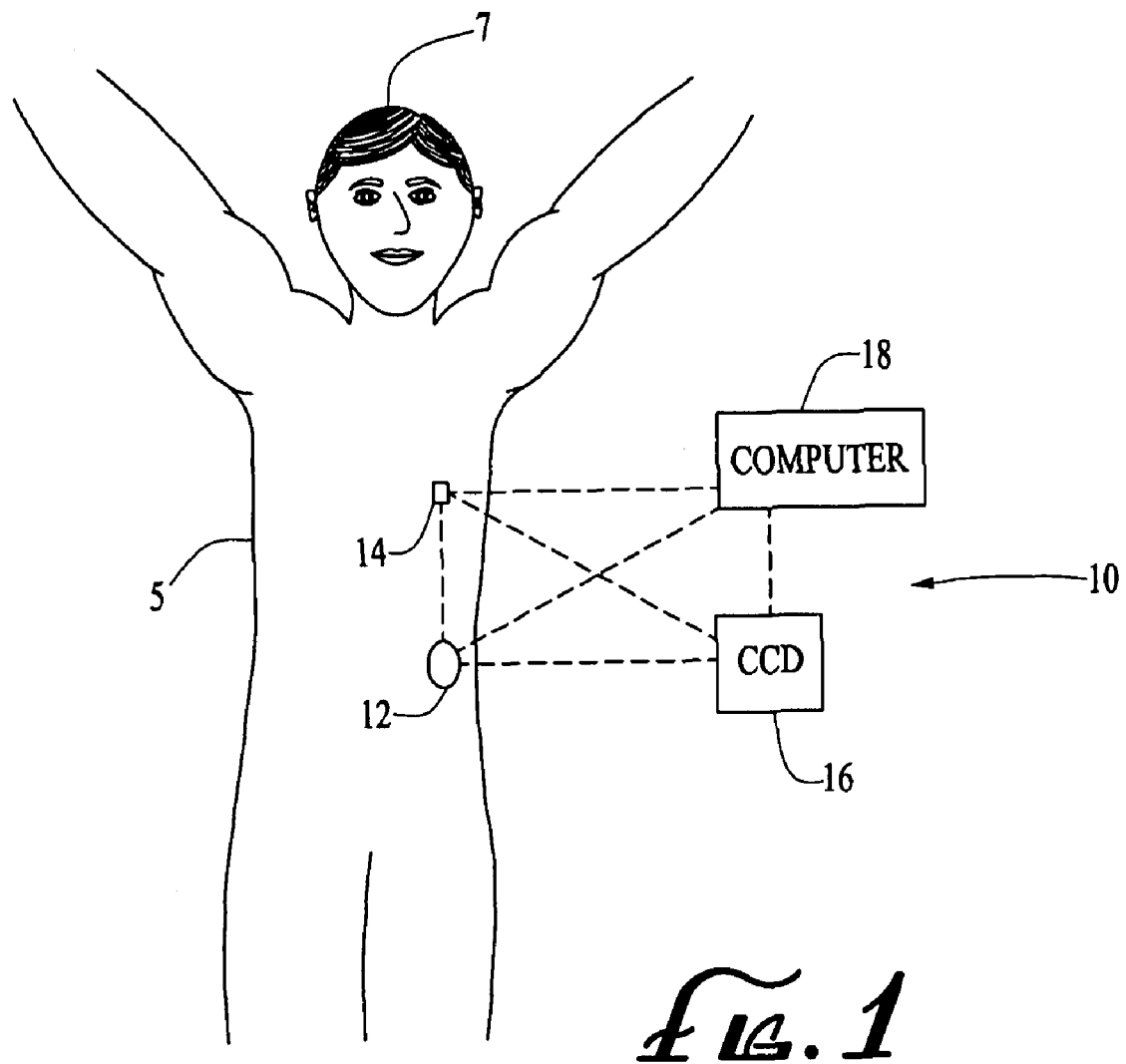
FIG. 1 illustrates a generalized representation of an infusion medium delivery system in accordance with an embodiment of the present invention.

FIG. 1 illustrates a generalized representation of an infusion medium delivery system 10 in accordance with an embodiment of the present invention. The infusion medium delivery system 10 includes a delivery device 12. The infusion medium delivery system 10 may further include a sensing device 14, a command control device (CCD) 16, and a computer 18. In various embodiments, the delivery device 12 and the sensing device 14 may be secured at desired locations on the body 5 of a patient or user 7. The locations at which the delivery device 12 and the sensing device 14 are secured to the body 5 of the user 7 in FIG. 1 are provided only as representative, non-limiting, examples.

The delivery device 12 is configured to deliver an infusion medium to the body 5 of the user 7. In various embodiments, the infusion medium includes a liquid, a fluid, a gel, or the like. In some embodiments, the infusion medium includes a medicine or a drug for treating a disease or a medical condition. For example, the infusion medium may include insulin for treating diabetes, or may include a drug for treating pain, cancer, a pulmonary disorder, HIV, or the like. In some embodiments, the infusion medium includes a nutritional supplement, a dye, a tracing medium, a saline medium, a hydration medium, or the like.

The sensing device 14 includes a sensor, a monitor, or the like, for providing sensor data or monitor data. In various embodiments, the sensing device 14 may be configured to sense a condition of the user 7. For example, the sensing device 14 may include electronics and enzymes reactive to a biological condition, such as a blood glucose level, or the like, of the user 7. In various embodiments, the sensing device 14 may be secured to the body 5 of the user 7 or embedded in the body 5 of the user 7 at a location that is remote from the location at which the delivery device 12 is secured to the body 5 of the user 7. In various other embodiments, the sensing device 14 may be incorporated within the delivery device 12.

Each of the delivery device 12, the sensing device 14, the CCD 16, and the computer 18 may include transmitter, receiver, or transceiver electronics that allow for communication with other components of the infusion medium delivery system 10. The sensing device 14 may be configured to transmit sensor data or monitor data to the delivery device 12. The sensing device 14 may also be configured to communicate with the CCD 16. The delivery device 12 may include electronics and software that are configured to analyze sensor data and to deliver the infusion medium to the body 5 of the user 7 based on the sensor data and/or preprogrammed delivery routines.

The CCD 16 and the computer 18 may include electronics and other components configured to perform processing, delivery routine storage, and to control the delivery device 12. By including control functions in the CCD 16 and/or the computer 18, the delivery device 12 may be made with more simplified electronics. However, in some embodiments, the delivery device 12 may include all control functions, and may operate without the CCD 16 and the computer 18. In various embodiments, the CCD 16 may be a portable electronic device. Also, in various embodiments, the delivery device 12 and/or the sensing device 14 may be configured to transmit data to the CCD 16 and/or the computer 18 for display or processing of the data by the CCD 16 and/or the computer 18. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

Figure 2:
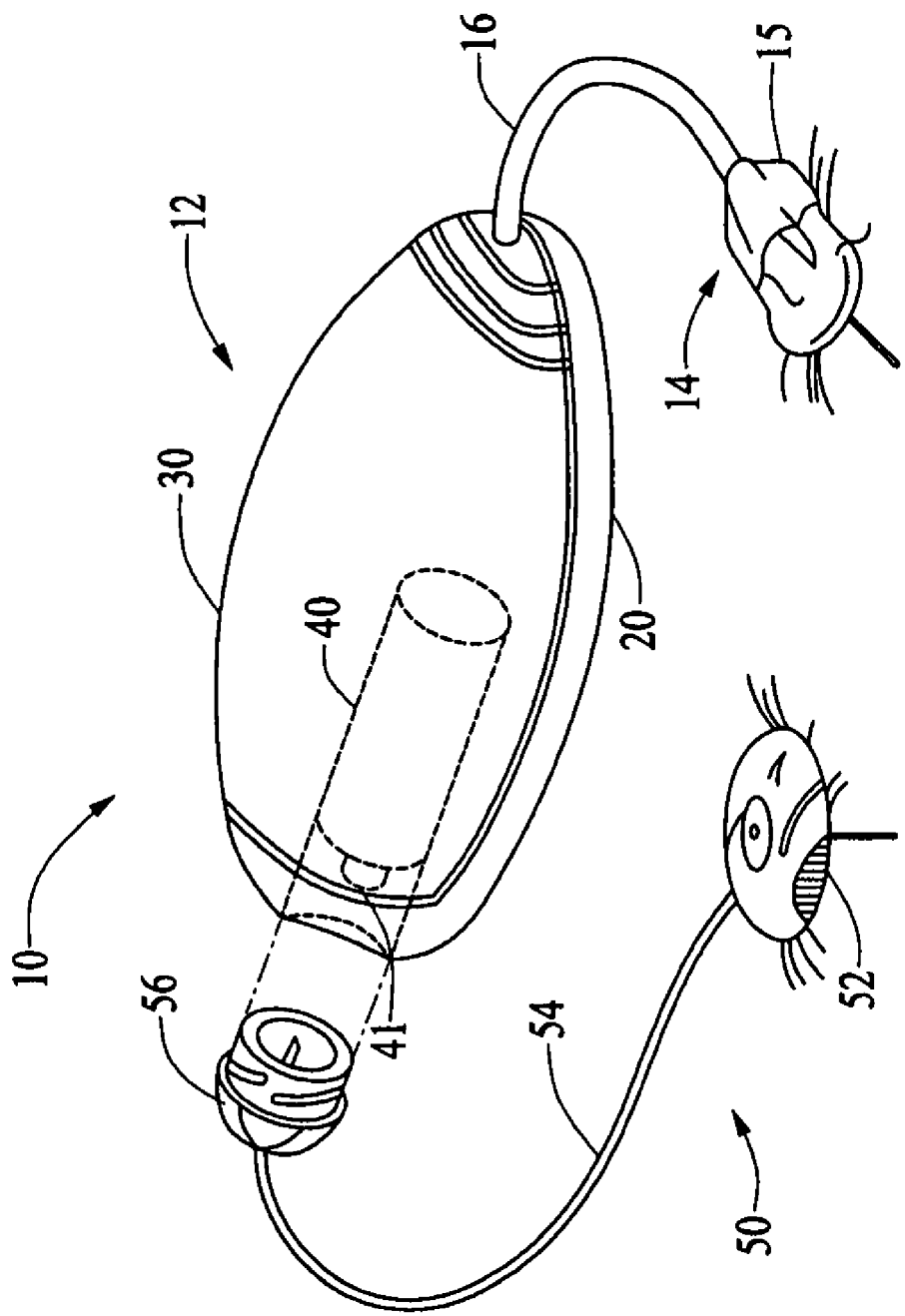
FIG. 2 illustrates an example of an infusion medium delivery system in accordance with an embodiment of the present invention.

FIG. 2 illustrates an example of the infusion medium delivery system 10 in accordance with an embodiment of the present invention. The infusion medium delivery system 10 in accordance with the embodiment illustrated in FIG. 2 includes the delivery device 12 and the sensing device 14. The delivery device 12 in accordance with an embodiment of the present invention includes a disposable housing 20, a durable housing 30, and a reservoir 40. The delivery device 12 may further include an infusion path 50.

Elements of the delivery device 12 that ordinarily contact the body of a user or that ordinarily contact an infusion medium during operation of the delivery device 12 may be considered as a disposable portion of the delivery device 12. For example, a disposable portion of the delivery device 12 may include the disposable housing 20 and the reservoir 40. The disposable portion of the delivery device 12 may be recommended for disposal after a specified number of uses.

On the other hand, elements of the delivery device 12 that do not ordinarily contact the body of the user or the infusion medium during operation of the delivery device 12 may be considered as a durable portion of the delivery device 12. For example, a durable portion of the delivery device 12 may include the durable housing 30, electronics (not shown in FIG. 2), a drive device having a motor and drive linkage (not shown in FIG. 2), and the like. Elements of the durable housing portion of the delivery device 12 are typically not contaminated from contact with the user or the infusion medium during normal operation of the delivery device 12 and, thus, may be retained for re-use with replaced disposable portions of the delivery device 12.

In various embodiments, the disposable housing 20 supports the reservoir 40 and has a bottom surface (facing downward and into the page in FIG. 2) that is configured to secure to the body of a user. An adhesive may be employed at an interface between the bottom surface of the disposable housing 20 and the skin of a user, so as to adhere the disposable housing 20 to the skin of the user. In various embodiments, the adhesive may be provided on the bottom surface of the disposable housing 20, with a peelable cover layer covering the adhesive material. In this manner, the cover layer may be peeled off to expose the adhesive material, and the adhesive side of the disposable housing 20 may be placed against the skin of the user.

The reservoir 40 is configured for containing or holding an infusion medium, such as, but not limited to insulin. In various embodiments, the reservoir 40 includes a hollow interior volume for receiving the infusion medium, such as, but not limited to, a cylinder-shaped volume, a tubular-shaped volume, or the like. In some embodiments, the reservoir 40 may be provided as a cartridge or canister for containing an infusion medium. In various embodiments, the reservoir 40 is able to be refilled with an infusion medium.

The reservoir 40 may be supported by the disposable housing 20 in any suitable manner. For example, the disposable housing 20 may be provided with projections or struts (not shown), or a trough feature (not shown), for holding the reservoir 40. In some embodiments, the reservoir 40 may be supported by the disposable housing 20 in a manner that allows the reservoir 40 to be removed from the disposable housing 20 and replaced with another reservoir. Alternatively, or in addition, the reservoir 40 may be secured to the disposable housing 20 by a suitable adhesive, a strap, or other coupling structure.

In various embodiments, the reservoir 40 includes a port 41 for allowing an infusion medium to flow into and/or flow out of the interior volume of the reservoir 40. In some embodiments, the infusion path 50 includes a connector 56, a tube 54, and a needle apparatus 52. The connector 56 of the infusion path 50 may be connectable to the port 41 of the reservoir 40. In various embodiments, the disposable housing 20 is configured with an opening near the port 41 of the reservoir 40 for allowing the connector 56 of the infusion path 50 to be selectively connected to and disconnected from the port 41 of the reservoir 40.

In various embodiments, the port 41 of the reservoir 40 is covered with or supports a septum (not shown in FIG. 2), such as a self-sealing septum, or the like. The septum may be configured to prevent an infusion medium from flowing out of the reservoir 40 through the port 41 when the septum is not pierced. Also, in various embodiments, the connector 56 of the infusion path 50 includes a needle for piercing the septum covering the port 41 of the reservoir 40 so as to allow the infusion medium to flow out of the interior volume of the reservoir 40. Examples of needle/septum connectors can be found in U.S. patent application Ser. No. 10/328,393 filed Dec. 22, 2003, and entitled "Reservoir Connector," which is incorporated herein by reference in its entirety. In other alternatives, non-septum connectors such as Luer locks, or the like may be used. In various embodiments, the needle apparatus 52 of the infusion path 50 includes a needle that is able to puncture skin of a user. Also, in various embodiments, the tube 54 connects the connector 56 with the needle apparatus 52 and is hollow, such that the infusion path 50 is able to provide a path to allow for the delivery of an infusion medium from the reservoir 40 to the body of a user.

The durable housing 30 of the delivery device 12 in accordance with various embodiments of the present invention includes a housing shell configured to mate with and secure to the disposable housing 20. The durable housing 30 and the disposable housing 20 may be provided with correspondingly shaped grooves, notches, tabs, or other suitable features, that allow the two parts to easily connect together, by manually pressing the two housings together, by twist or threaded connection, or other suitable manner of connecting the parts that is well known in the mechanical arts. In various embodiments, the durable housing 30 and the disposable housing 20 may be connected to each other using a twist action. The durable housing 30 and the disposable housing 20 may be configured to be separable from each other when a sufficient force is applied to disconnect the two housings from each other. For example, in some embodiments the disposable housing 20 and the durable housing 30 may be snapped together by friction fitting. In various embodiments, a suitable seal, such as an o-ring seal, may be placed along a peripheral edge of the durable housing 30 and/or the disposable housing 20, so as to provide a seal against water entering between the durable housing 30 and the disposable housing 20.

The durable housing 30 of the delivery device 12 may support a drive device (not shown in FIG. 2), including a motor and a drive device linkage portion, for applying a force to the infusion medium within the reservoir 40 to force the infusion medium out of the reservoir 40 and into an infusion path, such as the infusion path 50, for delivery to a user. For example, in some embodiments, an electrically driven motor may be mounted within the durable housing 30 with appropriate linkage for operatively coupling the motor to a plunger shaft (not shown in FIG. 2) connected to a piston (not shown in FIG. 2) that is within the reservoir 40 and to drive the piston in a direction to force the infusion medium out of the port 41 of the reservoir 40 and to the user. Also, in some embodiments, the motor may be controllable to reverse direction so as to move the plunger shaft and the piston to cause fluid to be drawn into the reservoir 40 from a patient. The motor may be arranged within the durable housing 30 and the reservoir 40 may be correspondingly arranged on the disposable housing 20, such that the operable engagement of the motor with the piston, through the appropriate linkage, occurs automatically upon the user connecting the durable housing 30 with the disposable housing 20 of the delivery device 12. Further examples of linkage and control structures may be found in U.S. patent application Ser. No. 09/813,660 filed Mar. 21, 2001, and entitled "Control Tabs For Infusion Devices And Methods Of Using The Same," which is incorporated herein by reference in its entirety.

In various embodiments, the durable housing 30 and the disposable housing 20 may be made of suitably rigid materials that maintain their shape, yet provide sufficient flexibility and resilience to effectively connect together and disconnect, as described above. The material of the disposable housing 20 may be selected for suitable compatibility with skin. For example, the disposable housing 20 and the durable housing 30 of the delivery device 12 may be made of any suitable plastic, metal, composite material, or the like. The disposable housing 20 may be made of the same type of material or a different material relative to the durable housing 30. In some embodiments, the disposable housing 20 and the durable housing 30 may be manufactured by injection molding or other molding processes, machining processes, or combinations thereof.

For example, the disposable housing 20 may be made of a relatively flexible material, such as a flexible silicone, plastic, rubber, synthetic rubber, or the like. By forming the disposable housing 20 of a material capable of flexing with the skin of a user, a greater level of user comfort may be achieved when the disposable housing 20 is secured to the skin of the user. Also, a flexible disposable housing 20 may result in an increase in site options on the body of the user at which the disposable housing 20 may be secured.

In the embodiment illustrated in FIG. 2, the delivery device 12 is connected to the sensing device 14 through a connection element 16 of the sensing device 14. The sensing device 14 may include a sensor 15 that includes any suitable biological or environmental sensing device, depending upon a nature of a treatment to be administered by the delivery device 12. For example, in the context of delivering insulin to a diabetes patient, the sensor 15 may include a blood glucose sensor, or the like.

The sensor 15 may be an external sensor that secures to the skin of a user or, in other embodiments, may be an implantable sensor that is located in an implant site within the body of the user. In further alternatives, the sensor may be included with as a part or along side the infusion cannula and/or needle, such as for example as shown in U.S. patent Ser. No. 11/149,119 filed Jun. 8, 2005, and entitled "Dual Insertion Set," which is incorporated herein by reference in its entirety. In the illustrated example of FIG. 2, the sensor 15 is an external sensor having a disposable needle pad that includes a needle for piercing the skin of the user and enzymes and/or electronics reactive to a biological condition, such as blood glucose level or the like, of the user. In this manner, the delivery device 12 may be provided with sensor data from the sensor 15 secured to the user at a site remote from the location at which the delivery device 12 is secured to the user.

While the embodiment shown in FIG. 2 includes a sensor 15 connected by the connection element 16 for providing sensor data to sensor electronics (not shown in FIG. 2) located within the durable housing 30 of the delivery device 12, other embodiments may employ a sensor 15 located within the delivery device 12. Yet other embodiments may employ a sensor 15 having a transmitter for communicating sensor data by a wireless communication link with receiver electronics (not shown in FIG. 2) located within the durable housing 30 of the delivery device 12. In various embodiments, a wireless connection between the sensor 15 and the receiver electronics within the durable housing 30 of the delivery device 12 may include a radio frequency (RF) connection, an optical connection, or another suitable wireless communication link. Further embodiments need not employ the sensing device 14 and, instead, may provide infusion medium delivery functions without the use of sensor data.

As described above, by separating disposable elements of the delivery device 12 from durable elements, the disposable elements may be arranged on the disposable housing 20, while durable elements may be arranged within a separable durable housing 30. In this regard, after a prescribed number of uses of the delivery device 12, the disposable housing 20 may be separated from the durable housing 30, so that the disposable housing 20 may be disposed of in a proper manner. The durable housing 30 may then be mated with a new (unused) disposable housing 20 for further delivery operation with a user.

Figure 3:
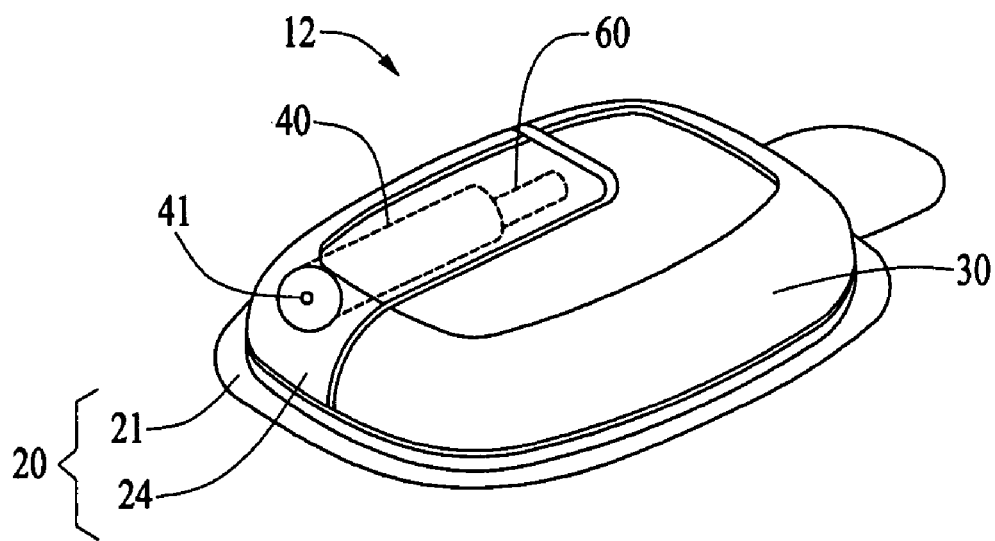
FIG. 3 illustrates an example of a delivery device in accordance with an embodiment of the present invention.

FIG. 3 illustrates an example of the delivery device 12 in accordance with another embodiment of the present invention. The delivery device 12 of the embodiment of FIG. 3 is similar to the delivery device 12 of the embodiment of FIG. 2. While the delivery device 12 in the embodiment illustrated in FIG. 2 provides for the durable housing 30 to cover the reservoir 40, the delivery device 12 in the embodiment of FIG. 3 provides for the durable housing 30 to secure to the disposable housing 20 without covering the reservoir 40. The delivery device 12 of the embodiment illustrated in FIG. 3 includes the disposable housing 20, and the disposable housing 20 in accordance with the embodiment illustrated in FIG. 3 includes a base 21 and a reservoir retaining portion 24. In one embodiment, the base 21 and reservoir retaining portion 24 may be formed as a single, unitary structure.

The base 21 of the disposable housing 20 is configured to be secured to the body of a user. The reservoir retaining portion 24 of the disposable housing 20 is configured to house the reservoir. The reservoir retaining portion 24 of the disposable housing 20 may be configured to have an opening to allow for the port 41 of the reservoir 40 to be accessed from outside of the reservoir retaining portion 24 while the reservoir 40 is housed in the reservoir retaining portion 24. The durable housing 30 may be configured to be attachable to and detachable from the base 21 of the disposable housing 20. The delivery device 12 in the embodiment illustrated in FIG. 3 includes a plunger shaft 60 that is connected to or that is connectable to a piston (not shown in FIG. 3) within the reservoir 40.

Figure 4:
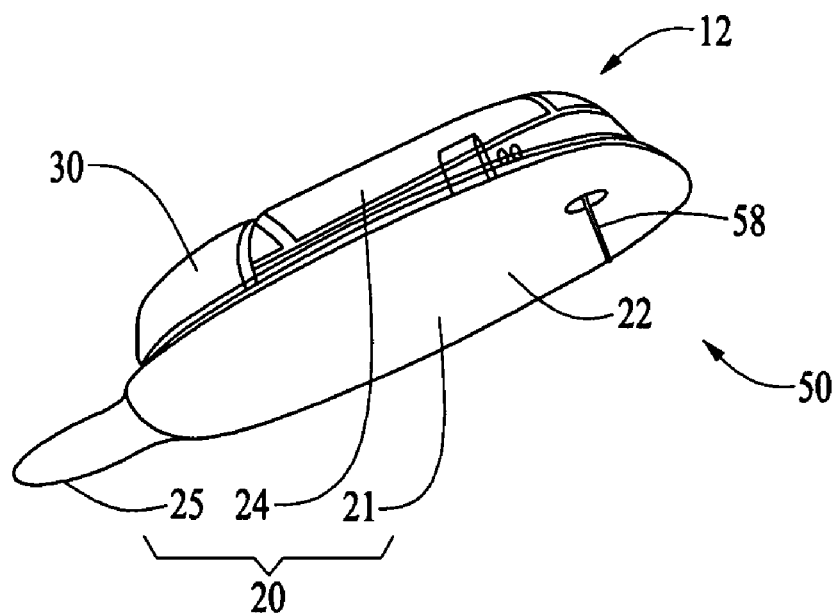
FIG. 4 illustrates a view of a delivery device in accordance with an embodiment of the present invention.

FIG. 4 illustrates another view of the delivery device 12 of the embodiment of FIG. 3. The delivery device 12 of the embodiment illustrated in FIG. 4 includes the disposable housing 20, the durable housing 30, and the infusion path 50. The disposable housing 20 in the embodiment of FIG. 4 includes the base 21, the reservoir retaining portion 24, and a peelable cover layer 25. The peelable cover layer 25 may cover an adhesive material on the bottom surface 22 of the base 21. The peelable cover layer 25 may be configured to be peelable by a user to expose the adhesive material on the bottom surface 22 of the base 21. In some embodiments, there may be multiple adhesive layers on the bottom surface 22 of the base 21 that are separated by peelable layers.

The infusion path 50 in accordance with the embodiment of the present invention illustrated in FIG. 4 includes the needle 58 rather than the connector 56, the tube 54, and the needle apparatus 52 as shown in the embodiment of FIG. 2. The base 21 of the disposable housing 20 may be provided with an opening or pierceable wall in alignment with a tip of the needle 58, to allow the needle 58 to pass through the base 21 and into the skin of a user under the base 21, when extended. In this manner, the needle 58 may be used to pierce the skin of the user and deliver an infusion medium to the user.

Alternatively, the needle 58 may be extended through a hollow cannula (not shown in FIG. 4), such that upon piercing the skin of the user with the needle 58, an end of the hollow cannula is guided through the skin of the user by the needle 58. Thereafter, the needle 58 may be removed, leaving the hollow cannula in place, with one end of the cannula located within the body of the user and the other end of the cannula in fluid flow connection with the infusion medium within the reservoir 40, to convey pumped infusion media from the reservoir 40 to the body of the user.

FIG. 5A illustrates a durable portion 8 of the delivery device 12 (refer to FIG. 3) in accordance with an embodiment of the present invention. FIG. 5B illustrates a section view of the durable portion 8 in accordance with an embodiment of the present invention. FIG. 5C illustrates another section view of the durable portion 8 in accordance with an embodiment of the present invention. With reference to FIGS. 5A, 5B, and 5C, in various embodiments, the durable portion 8 includes the durable housing 30, and a drive device 80. The drive device 80 includes a motor 84 and a drive device linkage portion 82. In various embodiments, the durable housing 30 may include an interior volume for housing the motor 84, the drive device linkage portion 82, other electronic circuitry, and a power source (not shown in FIGS. 5A, 5B, and 5C). Also, in various embodiments, the durable housing 30 is configured with an opening 32 for receiving a plunger shaft 60 (refer to FIG. 3). Also, in various embodiments, the durable housing 30 may include one or more connection members 34, such as tabs or the like, for connecting with the base 21 of the disposable housing 20 (refer to FIG. 3).

Figure 6A:
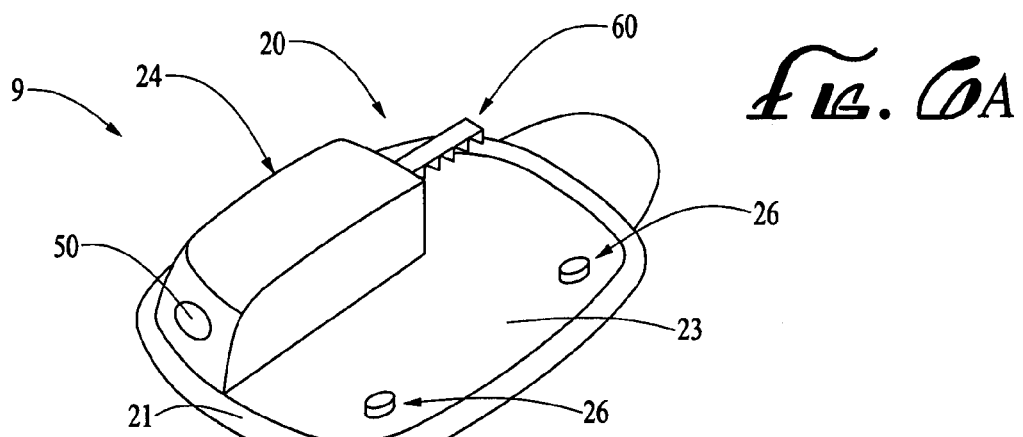
FIG. 6A illustrates a disposable portion of a delivery device in accordance with an embodiment of the present invention.
Figure 6B:
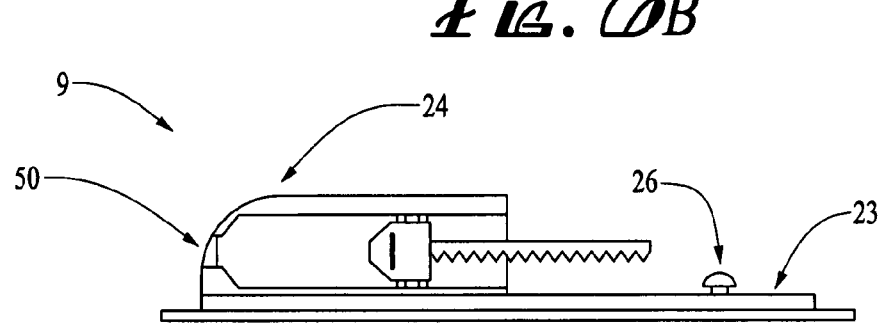
FIG. 6B illustrates a section view of a disposable portion of a delivery device in accordance with an embodiment of the present invention.
Figure 6C:
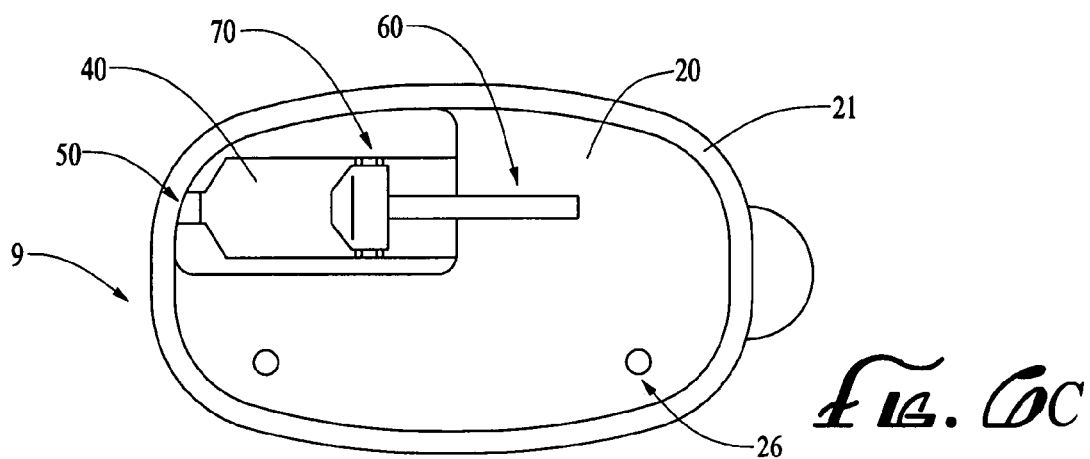
FIG. 6C illustrates a section view of a disposable portion of a delivery device in accordance with an embodiment of the present invention.

FIG. 6A illustrates a disposable portion 9 of the delivery device 12 (refer to FIG. 3) in accordance with an embodiment of the present invention. FIG. 6B illustrates a section view of the disposable portion 9 in accordance with an embodiment of the present invention. FIG. 6C illustrates another section view of the disposable portion 9 in accordance with an embodiment of the present invention. With reference to FIGS. 6A, 6B, and 6C, in various embodiments, the disposable portion 9 includes the disposable housing 20, the reservoir 40, the plunger shaft 60, and a piston 70. In some embodiments, the disposable housing 20 includes the base 21 and the reservoir retaining portion 24. In various embodiments, the base 21 includes a top surface 23 having one or more connection members 26, such as grooves or the like, for allowing connections with the one or more connection members 34 of embodiments of the durable housing 30 (refer to FIG. 5B).

In various embodiments, the reservoir 40 is housed within the reservoir retaining portion 24 of the disposable housing 20, and the reservoir 40 is configured to hold an infusion medium. Also, in various embodiments, the piston 70 is disposed at least partially within the reservoir 40 and is moveable within the reservoir 40 to allow the infusion medium to fill into the reservoir 40 and to force the infusion medium out of the reservoir 40.

In some embodiments, the plunger shaft 60 is connected to or is connectable to the piston 70. Also, in some embodiments, a portion of the plunger shaft 60 extends to outside of the reservoir retaining portion 24 of the disposable housing 20. In various embodiments, the plunger shaft 60 has a mating portion for mating with the drive device linkage portion 82 of the drive device 80 (refer to FIG. 5C). With reference to FIGS. 5C and 6C, in some embodiments, the durable housing 30 may be snap fitted onto the disposable housing 20, whereupon the drive device linkage portion 82 automatically engages the mating portion of the plunger shaft 60.

When the durable housing 30 and the disposable housing 20 are fitted together with the drive device linkage portion 82 engaging or mating with the plunger shaft 60, the motor 84 may be controlled to drive the drive device linkage portion 82 and, thus, move the plunger shaft 60 to cause the piston 70 to move within the reservoir 40. When the interior volume of the reservoir 40 is filled with an infusion medium and an infusion path 50 is provided from the reservoir 40 to the body of a user, the piston 70 may be moved within the reservoir 40 to force the infusion medium from the reservoir 40 and into the infusion path 50, so as to deliver the infusion medium to the body of the user.

In various embodiments, once the reservoir 40 has been sufficiently emptied or otherwise requires replacement, a user may simply remove the durable housing 30 from the disposable housing 20, and replace the disposable portion 9, including the reservoir 40, with a new disposable portion having a new reservoir. The durable housing 30 may be connected to the new disposable housing of the new disposable portion, and the delivery device including the new disposable portion may be secured to the skin of a user. In various other embodiments, rather than replacing the entire disposable portion 9 every time the reservoir 40 is emptied, the reservoir 40 may be refilled with an infusion medium. In some embodiments, the reservoir 40 may be refilled while remaining within the reservoir retaining portion 24 (refer to FIG. 6B) of the disposable housing 20. Also, in various embodiments, the reservoir 40 may be replaced with a new reservoir (not shown), while the disposable housing 20 may be re-used with the new reservoir. In such embodiments, the new reservoir may be inserted into the disposable portion 9.

With reference to FIGS. 3, 5A, and 6B, in various embodiments, the delivery device 12 includes reservoir status circuitry (not shown), and the reservoir 40 includes reservoir circuitry (not shown). In various embodiments, the reservoir circuitry stores information such as, but not limited to, at least one of (i) an identification string identifying the reservoir 40; (ii) a manufacturer of the reservoir 40; (iii) contents of the reservoir 40; and (iv) an amount of contents in the reservoir 40. In some embodiments, the delivery device 12 includes the reservoir status circuitry (not shown), and the reservoir status circuitry is configured to read data from the reservoir circuitry when the reservoir 40 is inserted into the disposable portion 9. In various embodiments, the reservoir status circuitry is further configured to store data to the reservoir circuitry after at least some of the contents of the reservoir 40 have been transferred out of the reservoir 40, so as to update information in the reservoir circuitry related to an amount of contents still remaining in the reservoir 40. In some embodiments, the reservoir status circuitry is configured to store data to the reservoir circuitry, so as to update information in the reservoir circuitry related to an amount of contents still remaining in the reservoir 40, when the reservoir 40 is inserted into the disposable portion 9. In some embodiments, the delivery device 12 includes the reservoir status circuitry (not shown) and the reservoir 40 includes the reservoir circuitry (not shown), and the reservoir status circuitry selectively inhibits use of the delivery device 12 or selectively provides a warning signal based on information read by the reservoir status circuitry from the reservoir circuitry.

Various systems, structures, and methods allowing for reservoir filling will now be discussed in more detail.

Figure 7:
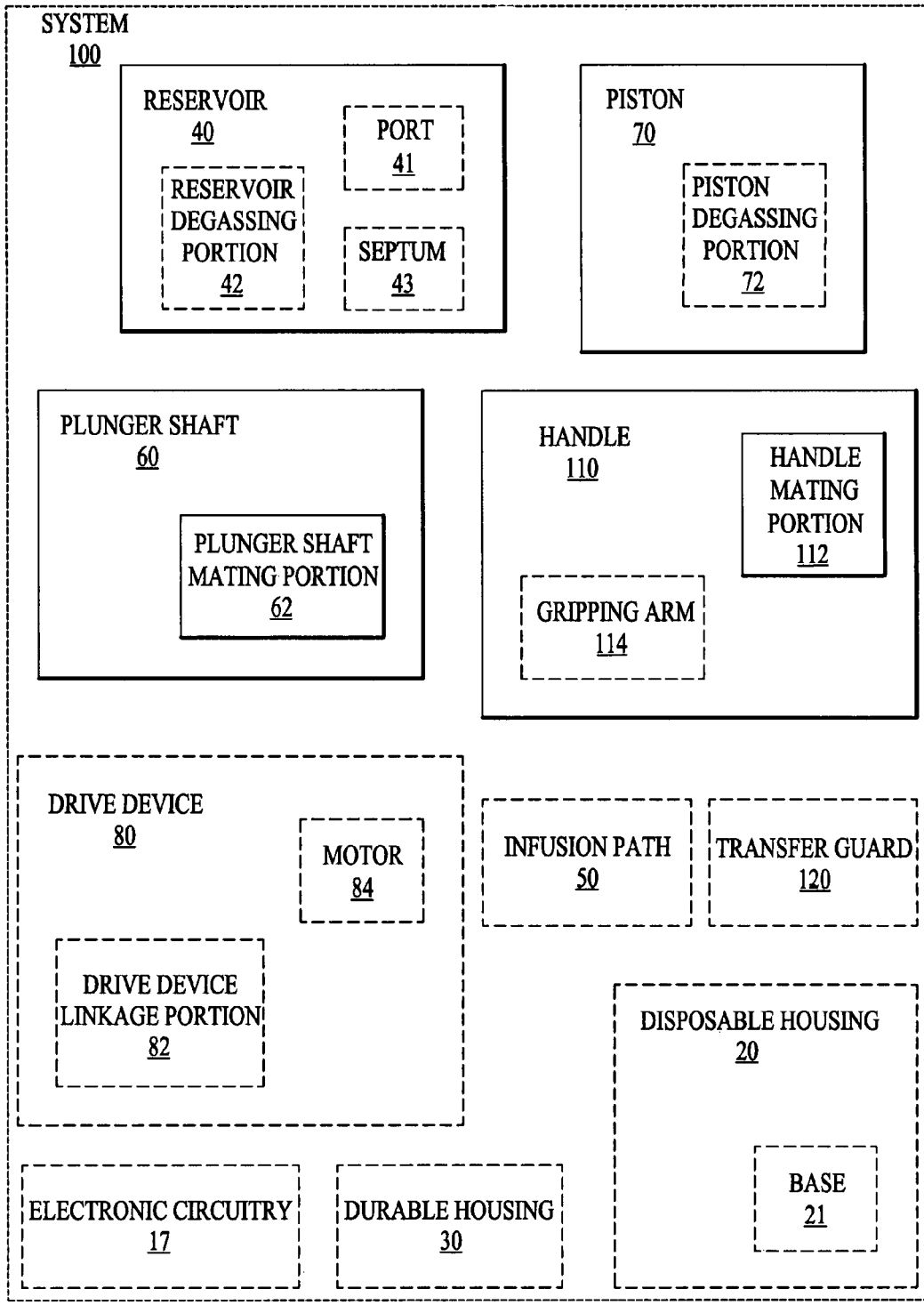
FIG. 7 illustrates a block diagram of a system in accordance with an embodiment of the present invention.

FIG. 7 illustrates a block diagram of a system 100 in accordance with an embodiment of the present invention. In various embodiments, the system 100 includes a reservoir filling system that allows for filling a reservoir, or the like. Also, in various embodiments, the system 100 includes a delivery device, such as the delivery device 12, or the like. In some embodiments, the system 100 includes an infusion medium delivery system, such as the infusion medium delivery system 10, or the like. In the embodiment illustrated in FIG. 7, the system 100 includes the reservoir 40, the piston 70, the plunger shaft 60, and a handle 110. Also, in the embodiment illustrated in FIG. 7, the plunger shaft 60 includes a plunger shaft mating portion 62, and the handle 110 includes a handle mating portion 112.

In various embodiments, the reservoir 40 is configured to hold an infusion medium. In various embodiments, the reservoir 40 is made of, for example, a suitable metal, plastic, ceramic, glass, composite material, or the like. In some embodiments, the reservoir 40 includes a canister or the like. Also, in some embodiments, the reservoir 40 has a hollow interior for containing or holding the infusion medium. The reservoir 40 may have a port 41 (refer to FIGS. 7 and 8) that allows for the infusion medium to flow into and/or out of the reservoir 40.

In some embodiments, the reservoir 40 includes a septum 43 (refer to FIGS. 7 and 9) that is positioned within an opening defined by the port 41 of the reservoir 40, where the septum 43 is capable of being pierced to allow the infusion medium to flow into the reservoir 40, and where the septum 43 is capable of holding the infusion medium within the reservoir 40 when the septum 43 is not pierced. In various embodiments, the septum 43 may be compressed around a needle (not shown in FIG. 7) that pierces the septum 43 for sealing against the needle and may be a self-sealing septum that re-seals itself, after removal of the needle. In some embodiments, the septum 43 may be compressed to provide a better seal around the needle. Also, in various embodiments, the septum 43 is formed of a suitable material such as, but not limited to, rubber, silicone rubber, polyurethane, or other materials that may be pierced by a needle and form a seal around the needle.

In various embodiments, the reservoir 40 includes a reservoir degassing portion 42. In such embodiments, the reservoir degassing portion 42 allows for gases to be released from the reservoir 40 while maintaining an infusion medium, such as liquids or the like, within the interior volume of the reservoir 40. In some embodiments, the reservoir degassing portion 42 includes a hydrophobic material or the like that will allow for air and other gases to pass through, but will not allow liquids, such as water, syringe deliverable insulin, or the like, to pass through. Also, in some embodiments, the reservoir degassing portion 42 includes a material such as a hydrophobic membrane, or the like, that is manufactured by Gore™. Such a reservoir degassing portion 42 may be positioned in any suitable position with respect to the reservoir 40 and may extend from an interior surface of the reservoir 40 to an exterior surface of the reservoir 40 to allow for gases to pass from the interior volume of the reservoir 40 to outside of the reservoir 40, so as to allow for degassing the interior volume of the reservoir 40. Examples of further structures that permit airflow, but that inhibit fluids can be found in U.S. patent application Ser. No. 10/328,393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety.

In various embodiments that include the reservoir degassing portion 42, once gases are removed from the interior volume of the reservoir 40 through the reservoir degassing portion 42, the reservoir 40 is sealed to prevent gases from re-entering the reservoir 40 and to prevent evaporation of an infusion medium in the reservoir 40. In some embodiments that include the reservoir degassing portion 42, the reservoir degassing portion 42 is used to degas the reservoir 40 with positive pressure and then is removed or covered to prevent evaporation of an infusion medium that is in the reservoir 40.

In various embodiments, the piston 70 (refer to FIGS. 7, 8, and 9) is disposed at least partially within the reservoir 40, where the piston 70 is moveable to allow the infusion medium to fill into the reservoir 40 and to force the infusion medium out of the reservoir 40. The piston 70 may be made of a suitably rigid material such as, but not limited to, metal, plastic, ceramic, glass, a composite material, or the like. In some embodiments, the piston 70 has a head with an outside diameter of slightly less than the inside diameter of the interior of the reservoir 40. In other embodiments, the piston 70 has a head with an outside diameter of slightly greater than or equal to the inside diameter of the interior of the reservoir 40, and the piston 70 may be compressible to fit within the reservoir 40. In various embodiments, the piston 70 extends partially into the interior of the reservoir 40 from an opposite side of the reservoir 40 relative to the port 41 of the reservoir 40.

Figure 9:
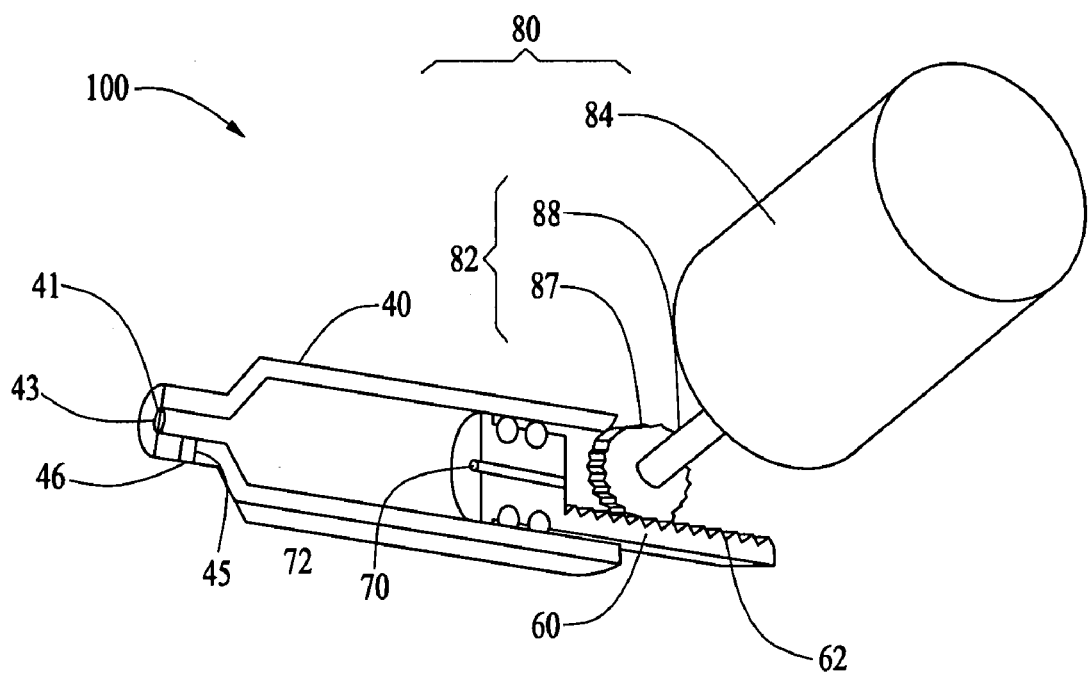
FIG. 9 illustrates a portion of an embodiment of a system in accordance with another embodiment of the present invention.

In various embodiments, the piston 70 includes a piston degassing portion 72 (refer to FIGS. 7 and 9). In such embodiments, the piston degassing portion 72 allows for gases to be released from the reservoir 40 through an opening in the piston 70 while maintaining an infusion medium, such as liquids or the like, within the interior volume of the reservoir 40. In some embodiments, the piston degassing portion 72 includes a hydrophobic material or the like that will allow for air and other gases to pass through, but will not allow liquids, such as water, syringe deliverable insulin, or the like, to pass through. Also, in some embodiments, the piston degassing portion 72 includes a material such as a hydrophobic membrane, or the like, that is manufactured by Gore™. Examples of structures that permit air-flow, but that inhibit fluids can be found in U.S. patent application Ser. No. 10/328,393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety. Such a piston degassing portion 72 may be positioned in any suitable position with respect to the piston 70 and may extend from a first surface of the piston 70 that faces the interior volume of the reservoir 40 to a second surface of the piston 70 that is opposite the first surface, to allow for gases to pass from the interior volume of the reservoir 40 to outside of the reservoir 40, so as to allow for degassing the interior volume of the reservoir 40.

In various embodiments that include the piston degassing portion 72, once gases are removed from the interior volume of the reservoir 40 through the piston degassing portion 72, the piston 70 is sealed to prevent gases from re-entering the reservoir 40 and to prevent evaporation of an infusion medium in the reservoir 40. In some embodiments that include the piston degassing portion 72, the piston degassing portion 72 is used to degas the reservoir 40 with positive pressure and then is removed or covered to prevent evaporation of an infusion medium that is in the reservoir 40.

In various embodiments, the plunger shaft 60 (refer to FIGS. 7, 8, and 9) is connected to the piston 70. In some embodiments, the plunger shaft 60 is formed as a single unit with the piston 70. In various other embodiments, the plunger shaft 60 is attached to the piston 70 by, for example, an adhesive, a screw, joining engagement portions of the plunger shaft 60 and the piston 70, or the like. The plunger shaft 60 may be made of a suitably rigid material such as, but not limited to, metal, plastic, ceramic, glass, a composite material, or the like.

In some embodiments, the plunger shaft 60 includes the plunger shaft mating portion 62. In such embodiments, the plunger shaft mating portion 62 is configured to allow for mating with a linkage portion of a drive device, such as the drive device linkage portion 82 of the drive device 80 (refer to FIGS. 7, 8, and 9). In various embodiments, the drive device 80 allows for driving the plunger shaft 60 so as to move the piston 70 to force the infusion medium out of the reservoir 40 when the drive device linkage portion 82 of the drive device 80 is mated with the plunger shaft mating portion 62 of the plunger shaft 60. In some embodiments, the plunger shaft mating portion 62 is provided with threads, keys, key slots, or the like, that are configured to operatively engage or mate with corresponding threads, keys, key slots, or the like, of the drive device linkage portion 82. In some embodiments, the plunger shaft 60 includes a partial nut, a lead screw, or the like.

The handle 110 includes the handle mating portion 112 (refer to FIGS. 7, 12, 13, and 30). The handle 110 may be made of a suitably rigid material such as, but not limited to, metal, plastic, ceramic, glass, a composite material, or the like. The handle mating portion 112 of the handle 110 is configured to allow for mating with the plunger shaft mating portion 62 of the plunger shaft 60. In some embodiments, the handle mating portion 112 is provided with threads, keys, key slots, or the like, that are configured to operatively engage or mate with corresponding threads, keys, key slots, or the like, of the plunger shaft mating portion 62. In various embodiments, the handle mating portion 112 of the handle 110 includes a lead screw, a partial nut, or the like.

The handle 110 is capable of being used by a user to move the plunger shaft 60 so as to move the piston 70 to allow the infusion medium to flow or fill into the reservoir 40 when the handle mating portion 112 of the handle 110 is mated with the plunger shaft mating portion 62 of the plunger shaft 60. The handle mating portion 112 of the handle 110 may be mated with the plunger shaft mating portion 62 of the plunger shaft 60 when the drive device linkage portion 82 of the drive device 80 has been disconnected or disengaged from the plunger shaft mating portion 62 of the plunger shaft 60.

In various embodiments, the handle 110 further includes a gripping arm 114 for gripping the plunger shaft 60 when the handle mating portion 112 of the handle 110 is mated with the plunger shaft mating portion 62 of the plunger shaft 60. In some embodiments, the plunger shaft mating portion 62 includes a partial nut, the handle mating portion 112 includes a threaded interface, and the gripping arm 114 extends from the handle mating portion 112 of the handle 110. In such embodiments, the handle mating portion 112 may be mated with the plunger shaft mating portion 62 and then rotated to cause the gripping arm 114 to grip the plunger shaft 60 between the gripping arm 114 and the handle mating portion 112 of the handle 110.

Figure 8:
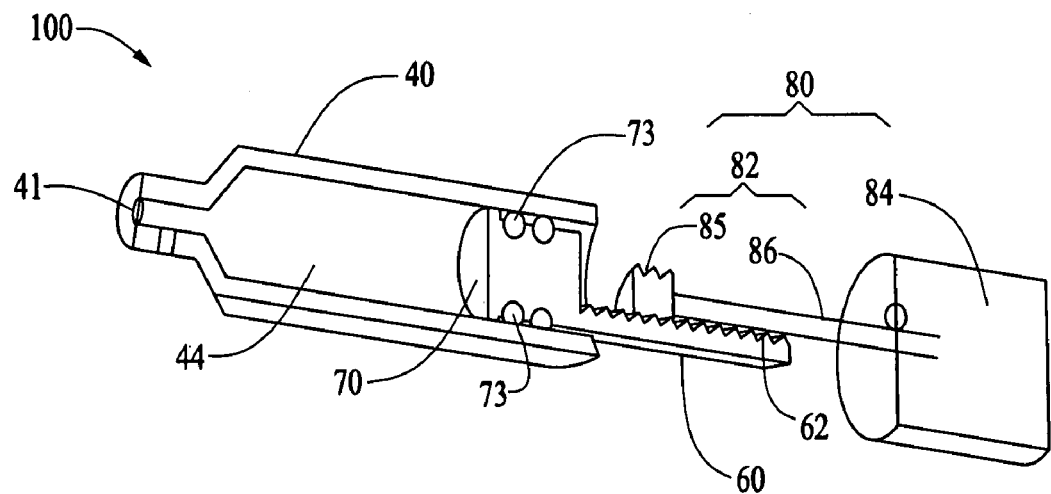
FIG. 8 illustrates a portion of an embodiment of a system in accordance with an embodiment of the present invention.

In various embodiments, the system 100 further includes the drive device 80 (refer to FIGS. 7, 8, and 9). In some embodiments, the drive device 80 includes the drive device linkage portion 82 and the motor 84. The motor 84 may be mechanically coupled to the drive device linkage portion 82 to drive the drive device linkage portion 82 in a controlled manner. For example, the drive device linkage portion 82 may include a threaded lead screw, and the motor 84 may drive the lead screw in a rotary motion about its longitudinal axis. The drive device linkage portion 82 may include one or more suitable gears, belts, chains, drive shafts, or other linkage structures for coupling to the motor 84. Examples of suitable motors that may be used for the motor 84 include, but are not limited to, a DC motor, a flat or pancake DC motor, a servo motor, a stepper motor, an electronically commutated motor, a rotary piezo-electrically actuator motor, and the like. In some embodiments, the drive device linkage portion 82 is provided with threads, keys, key slots, or the like, that are configured to operatively engage or mate with corresponding threads, keys, key slots, or the like, of the plunger shaft mating portion 62. In various embodiments, the drive device linkage portion 82 includes a lead screw, a partial nut, or the like.

In some embodiments, the system 100 further includes the infusion path 50. In some embodiments, the infusion path 50 includes the connector 56, the tube 54, and the needle apparatus 52 as illustrated in FIG. 2, for connecting to the port 41 of the reservoir 40 and for providing a path to deliver the infusion medium from the reservoir 40 to the body of a user. Also, in various embodiments, the infusion path 50 includes the needle 58 as illustrated in FIG. 4 for providing a path to deliver the infusion medium from the reservoir 40 to the body of the user through an opening in the base of a disposable housing. In various embodiments, the port 41 of the reservoir 40 is connectable to the infusion path 50 to allow for delivering the infusion medium from the reservoir to the body of a particular user, where the port 41 is also connectable to a transfer path, such as a transfer guard 120 or the like, to allow the infusion medium to be transferred into the reservoir 40 from an infusion medium container (not shown in FIG. 7), such as a vial, a canister, or the like.

In various embodiments, the system 100 further includes the transfer device, referred to herein as a transfer guard 120 (refer to FIGS. 7 and 10-13). In some embodiments, the transfer guard 120 is connectable to the port 41 of the reservoir 40 for providing a path to allow the infusion medium to be transferred from an infusion medium container to the reservoir 40. In various embodiments, the transfer guard 120 is configured like one or more of the embodiments of the transfer guard as disclosed in U.S. Pat. No. 6,591,876, entitled "Needle Safe Transfer Guard", the contents of which are incorporated by reference herein. In some embodiments, the transfer guard 120 includes a degassing portion (not shown) that allows for the reservoir 40 to be filled with an infusion medium and then allows for the reservoir 40 to be degassed, and then is removed to allow the reservoir 40 to be sealed.

In some embodiments, the system 100 further includes the disposable housing 20. In various embodiments, the disposable housing includes the base 21. Also, in various embodiments, the reservoir 40, the piston 70, and the plunger shaft 60 are supported by the base 21 of the disposable housing 20. In some embodiments, the base 21 of the disposable housing 20 is adapted to be secured to a user, such as with an adhesive, or the like. Also, in some embodiments, the reservoir 40 is connected to the base 21 of the disposable housing 20.

In various embodiments, the system 100 further includes the durable housing 30. In some embodiments, the drive device 80 and electronic circuitry 17 are housed or contained within the durable housing 30. In various embodiments of the system 100, the durable housing 30 and the disposable housing 20 are configured as in the embodiment of the delivery device 12 illustrated in FIG. 2. In various other embodiments of the system 100, the durable housing 30 and the disposable housing 20 are configured as in the embodiment of the delivery device 12 illustrated in FIG. 3.

In some embodiments, the system 100 further includes the electronic circuitry 17. In various embodiments, the electronic circuitry 17 may be configured to control the motor 84 according to a desired infusion medium delivery program or profile. A delivery program or profile may be stored within a suitable electronic storage medium (not shown) located within the durable housing 30 and/or may be communicated to the electronic circuitry 17 from other sources, such as the CCD 16 or the sensing device 14 or the computer 18 shown in FIG. 1. Alternatively, or in addition, the electronic circuitry 17 may control the motor 84 to deliver one or more discrete volumes of the infusion medium in response to delivery demand control signals generated within the system 100 or communicated to the system 100 from other sources. In various embodiments, the electronic circuitry 17 may be housed or contained within the durable housing 30.

FIG. 8 illustrates a portion of an embodiment of the system 100 in accordance with an embodiment of the present invention. In the embodiment illustrated in FIG. 8, the reservoir 40 has the port 41, and the piston 70 is disposed within the reservoir 40. In various embodiments, the reservoir 40 defines an infusion medium retaining interior volume or portion 44 for holding or containing an infusion medium. In some embodiments, one or more seals 73 may be provided around an outer peripheral surface of the piston 70, to inhibit a passage of the infusion medium across the piston 70 from the infusion medium retaining interior portion 44 of the reservoir 40 to outside of the reservoir 40.

In various embodiments, the seals 73 may include one or more o-ring seals or other suitable seal structures and may be made of any suitable material, including but not limited to, rubber, silicone rubber, polyurethane or other plastic material, metal, composite material, or the like. In some embodiments, the seals 73 may provide sufficient frictional force between the piston 70 and an interior surface of the reservoir 40 to inhibit rotation of the piston 70 with respect to the reservoir 40. Also, in various embodiments, additional structure may be provided to inhibit rotation of the piston 70 with respect to the reservoir 40 including, but not limited to, one or more keys, projections, or shaped portions on the piston 70 that fit within corresponding one or more grooves along a length of the interior surface of the reservoir 40, or vice versa. For example, the interior surface of the reservoir 40 may have a groove, and the piston 70 may have a corresponding projection that fits slidably within the groove, such that the piston 70 is able to slide within the reservoir 40, but is not able to rotate within the reservoir 40. In yet further embodiments, the cross sectional shape of the piston 70 and of the reservoir 40 may be non-circular, such as, but not limited to, oval, to inhibit rotation of the piston 70 with respect to the reservoir 40. Such a non-circular cross-sectional shape of the piston 70 and of the reservoir 40 may also minimize an overall height the piston 70 and the reservoir 40.

In the embodiment illustrated in FIG. 8, the plunger shaft 60 is formed as a single unit with the piston 70. Also, in the embodiment illustrated in FIG. 8, the plunger shaft 60 has the plunger shaft mating portion 62 that includes a partial nut that is threaded along the longitudinal direction of the plunger shaft 60. Moreover, in the embodiment illustrated in FIG. 8, the drive device linkage portion 82 of the drive device 80 includes a rotatably driven drive shaft 86 on which a drive screw 85 is mounted. In various embodiments, the drive screw 85 of the drive device linkage portion 82 is threaded. During operation of the embodiment illustrated in FIG. 8, the drive screw 85 of the drive device linkage portion 82 is arranged to mate with the plunger shaft mating portion 62 and, upon rotation of the drive shaft 86 by the motor 84, the drive screw 85 is rotated to cause a linear movement of the plunger shaft 60 relative to the reservoir 40 and, as a result, the piston 70 is moved within the reservoir 40.

In various embodiments, the reservoir 40 may be supported by the base 21 of the disposable housing 20, while the motor 84 along with the drive shaft 86 and the drive screw 85 may be supported within the durable housing 30. In such embodiments, when the durable housing 30 is removed from the disposable housing 20, the drive screw 85 may be easily disengaged or disconnected from the plunger shaft mating portion 62 of the plunger shaft 60 by simply lifting the drive screw 85 off of the plunger shaft mating portion 62. Also, in various embodiments, the plunger shaft 60 is positioned with respect to the disposable housing 20 such that when the durable housing 30 is connected to the disposable housing 30, the drive screw 85 automatically mates with the plunger shaft mating portion 62 of the plunger shaft 60.

FIG. 9 illustrates a portion of an embodiment of the system 100 in accordance with another embodiment of the present invention. In the embodiment illustrated in FIG. 9, the reservoir 40 has the port 41 and further has a second port 45. In the embodiment of FIG. 9, the septum 43 is located within the port 41, and a second septum 46 is located within the second port 45. In various embodiments, the port 41 is connectable to an embodiment of the infusion path 50 that includes the connector 56, the tube 54, and the needle apparatus 52 (refer to FIG. 2). Also, in various embodiments, the second port 45 is connectable to an embodiment of the infusion path 50 that includes the needle 58 (refer to FIG. 4). In some embodiments, the reservoir 40 is filled with an infusion medium through the port 41 and the infusion medium is forced out of the reservoir 40 through the second port 45. The embodiment of the reservoir 40 illustrated in FIG. 9 may be said to be a multi-port reservoir, because the reservoir 40 has two ports.

In the embodiment illustrated in FIG. 9, the piston 70 is disposed within the reservoir 40, and the plunger shaft 60 is formed as a single unit with the piston 70. In the embodiment illustrated in FIG. 9, the plunger shaft 60 has the plunger shaft mating portion 62 that includes a threaded rack that is threaded along the longitudinal direction of the plunger shaft 60. Moreover, in the embodiment illustrated in FIG. 9, the drive device linkage portion 82 of the drive device 80 includes a rotatably driven drive shaft 88 on which a pinion gear 87 is fixedly mounted for rotation with rotation of the drive shaft 88. During operation of the embodiment illustrated in FIG. 9, the pinion gear 87 of the drive device linkage portion 82 is arranged to mate with the plunger shaft mating portion 62 and, upon rotation of the drive shaft 88 by the motor 84, the pinion gear 87 is rotated to cause a linear movement of the plunger shaft 60 relative to the reservoir 40 and, as a result, the piston 70 is moved within the reservoir 40.

In various embodiments, the reservoir 40 may be supported by the base 21 of the disposable housing 20, while the motor 84 along with the drive shaft 88 and the pinion gear 87 may be supported within the durable housing 30. In such embodiments, when the durable housing 30 is removed from the disposable housing 20, the pinion gear 87 may be easily disengaged or disconnected from the plunger shaft mating portion 62 of the plunger shaft 60 by simply lifting the pinion gear 87 off of the plunger shaft mating portion 62. Also, in various embodiments, the plunger shaft 60 is positioned with respect to the disposable housing 20 such that when the durable housing 30 is connected to the disposable housing 30, the pinion gear 87 automatically mates with the plunger shaft mating portion 62 of the plunger shaft 60.

FIG. 10 illustrates another portion of an embodiment of the system 100 in accordance with an embodiment of the present invention. In the embodiment illustrated in FIG. 10, the system 100 includes the reservoir 40, the plunger shaft 60, and the transfer guard 120. In various embodiments, the system 100 further includes an infusion medium container 130. The infusion medium container 130 allows for holding an infusion medium. In various embodiments, the infusion medium container 130 includes a vial, a canister, or the like. Also, in various embodiments, the infusion medium container 130 is made of a suitable material such as, but not limited to, metal, plastic, ceramic, glass, composite material, or the like. In some embodiments, the infusion medium container 130 is configured with an opening, and a septum 132 that is able to be pierced by a needle is located within or over the opening in the infusion medium container 130, and the infusion medium is able to flow out of the opening in the infusion medium container 130 when the septum 132 is pierced.

In various embodiments, the transfer guard 120 includes a supply adapter 122, a receiver adapter 124, a support structure 126, and an infusion medium conducting element 128. In some embodiments, the supply adapter 122 is adapted to be mated with the infusion medium container 130. Also, in some embodiments, the receiver adapter 124 is adapted to be mated with the reservoir 40. In various embodiments, the support structure 126 is coupled between the supply adapter 122 and the receiver adapter 124, where the support structure 126 is configured to allow movement of the supply adapter 122 and the receiver adapter 124 from a first more distant position relative to each other to a second closer position relative to each other.

Also, in various embodiments, the infusion medium conducting element 128 includes a needle or the like that extends from the supply adapter 122 to the receiver adapter 124. In some embodiments, the supply adapter 122 and the receiver adapter 124 are further adapted to substantially protect the corresponding tips of the infusion medium conducting element 128, such as needle tips, from contact with a user. In various embodiments, the infusion medium conducting element 128 is able to pierce the septum 132 of the infusion medium container 130 and is able to pierce the septum 43 of the reservoir 40, so as to establish a transfer path for transferring an infusion medium from the infusion medium container 130 to the reservoir 40.

FIG. 11 illustrates a portion of an embodiment of the system 100 in accordance with the embodiment shown in FIG. 10, where the transfer element 120 has been mated with the infusion medium container 130 and with the reservoir 40. As is illustrated in FIG. 11, in various embodiments, the supply adapter 122 is able to mate with the infusion medium container 130 and the receiver adapter 124 is able to mate with the reservoir 40, such that the infusion medium conducting element provides a transfer path from the infusion medium container 130 to the reservoir 40. In some embodiments, the reservoir 40 includes an opening out of which the plunger shaft 60 extends, where the receiver adapter 124 of the transfer guard 120 is connectable to an opposite side of the reservoir 40 from a side of the reservoir 40 that has the opening out of which the plunger shaft 60 extends.

Figure 12:
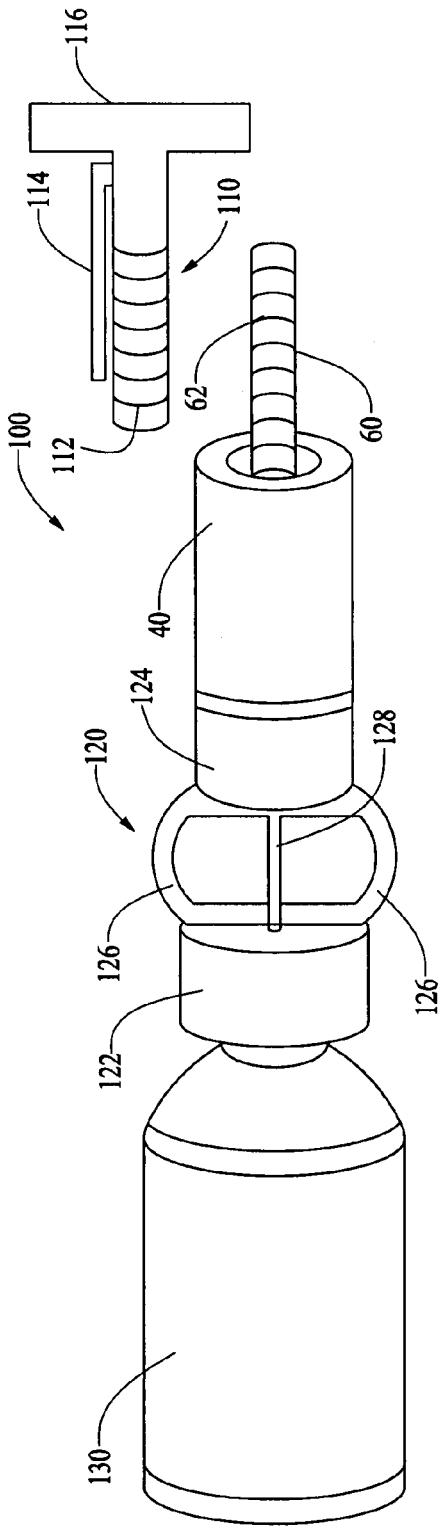
FIG. 12 illustrates another portion of an embodiment of a system in accordance with an embodiment of the present invention.

FIG. 12 illustrates another portion of an embodiment of the system 100 in accordance with an embodiment of the present invention. In the portion of the system 100 illustrated in the embodiment of FIG. 12, the system 100 includes the infusion medium container 130, the transfer guard 120, the reservoir 40, the plunger shaft 60, and the handle 110. In the embodiment of the system 100 illustrated in FIG. 12, the plunger shaft mating portion 62 of the plunger shaft 60 includes a threaded partial nut, and the handle mating portion 112 of the handle 110 includes a threaded interface. The handle mating portion 112 of the handle 110 is configured to be mated with the plunger shaft mating portion 62 of the plunger shaft. In various embodiments, the handle mating portion 112 is mated with the plunger shaft mating portion 62 by placing the handle mating portion 112 on the plunger shaft mating portion 62.

Placing the handle mating portion 112 on the plunger shaft mating portion 62 is only an example of a method of mating the handle 110 with the plunger shaft 60, and various other embodiments of the present invention are not limited to such a mating method. For example, various other embodiments may provide for the handle mating portion 112 and the plunger shaft mating portion 62 to be keyed, and for the handle mating portion 112 and the plunger shaft mating portion 62 to be mated by joining the keyed portions of each together. Also, various other embodiments may provide for the handle mating portion 112 to include a protrusion and for the plunger shaft mating portion 62 to include a corresponding groove so that the handle mating portion 112 is able to be mated with the plunger shaft mating portion 62 by placing the protrusion of the handle mating portion 112 in the groove of the plunger shaft mating portion 62. Various other mating methods are also possible.

In various embodiments, the handle 110 includes the gripping arm 114 for gripping the plunger shaft 60 when the handle mating portion 112 of the handle 110 is mated with the plunger shaft mating portion 62 of the plunger shaft 60. Also, in various embodiments, the handle 110 further includes a bar 116 connected to the handle mating portion 112, where the bar 116 is able to be gripped by the hand of a user to pull or push the handle 110 when the handle mating portion 112 is mated with the plunger shaft mating portion 62.

Figure 30:
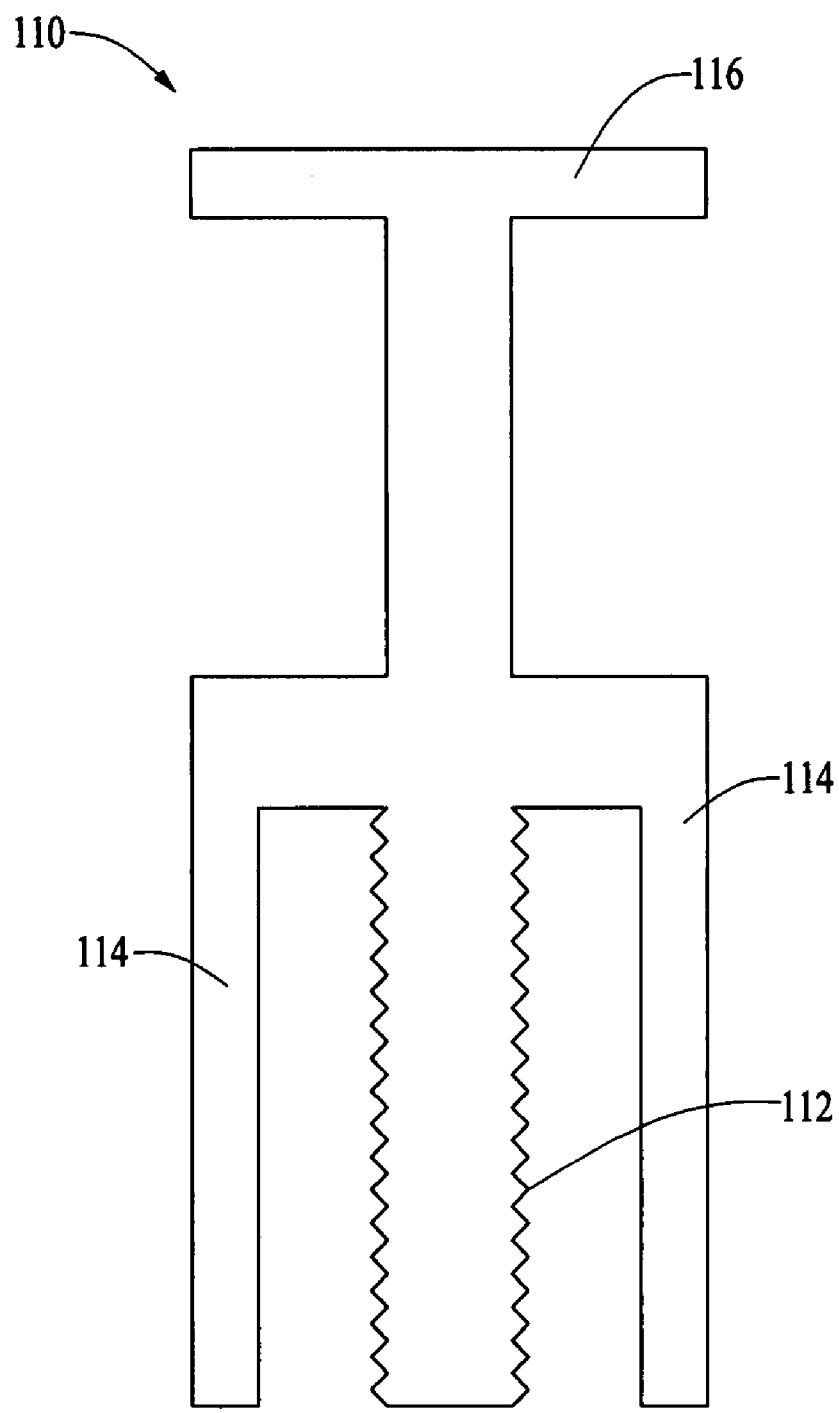
FIG. 30 illustrates an embodiment of a handle in accordance with an embodiment of the present invention.

FIG. 30 illustrates another embodiment of the handle 110 in accordance with an embodiment of the present invention. The handle 110 illustrated in FIG. 30 includes the bar 116, the handle mating portion 112, and the gripping arm 114. The gripping arm 114 of the embodiment of the handle 110 in FIG. 30 is a skirt or sleeve that surrounds the handle mating portion 112.

Figure 13:
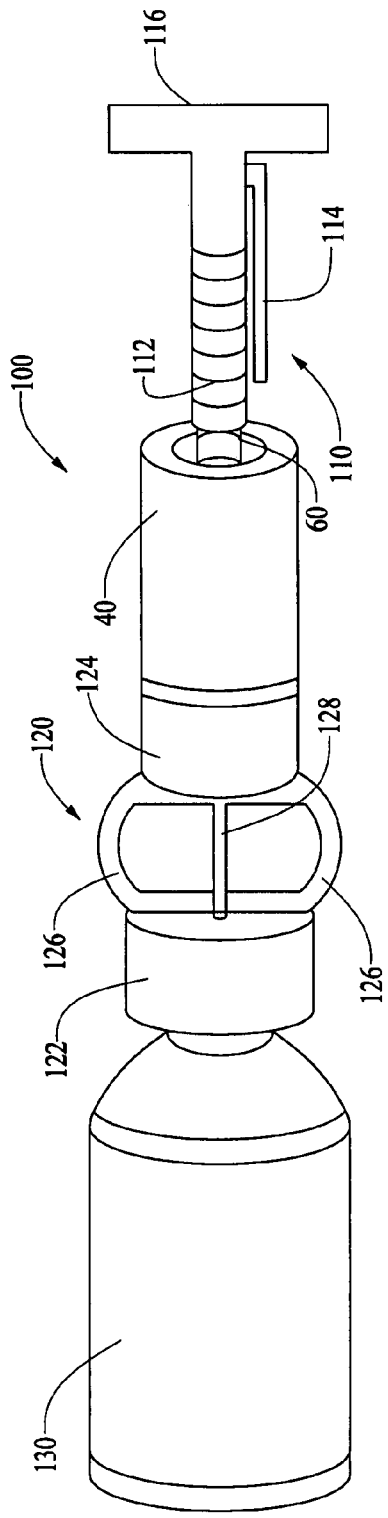
FIG. 13 illustrates a portion of an embodiment of a system in accordance with an embodiment of the present invention.

FIG. 13 illustrates a portion of an embodiment of the system 100 in accordance with the embodiment shown in FIG. 12, where the handle mating portion 112 of the handle 110 has been mated with the plunger shaft mating portion 62 of the plunger shaft 60. As is illustrated in FIG. 13, in various embodiments, the handle mating portion 112 of the handle 110 is threaded and the plunger shaft mating portion 62 of the plunger shaft 60 is threaded, such that the handle mating portion 112 is able to mate with the plunger shaft mating portion 62 when the handle mating portion 112 is placed on the plunger shaft mating portion 62. In some embodiments, when the handle mating portion 112 is mated with the plunger shaft mating portion 62, the gripping arm 114 of the handle 110 is able to surround a perimeter of the plunger shaft 60 by 180° or more around the perimeter. In other embodiments, when the handle mating portion 112 is mated with the plunger shaft mating portion 62, the gripping arm 114 of the handle 110 is able to surround a perimeter of the plunger shaft 60 by only less than 180° around the perimeter. In some embodiments, when the handle mating portion 112 is mated with the plunger shaft mating portion 62, the gripping arm 114 of the handle 110 is able to surround a perimeter of the plunger shaft 60 by 360° around the perimeter.

In various embodiments, the handle 110 may be rotated when the handle mating portion 112 is mated with the plunger shaft mating portion 62 such that the handle 110 is positioned in a location where at least a portion of the plunger shaft 60 is located between the gripping arm 114 and at least a portion of the handle mating portion 112. Also, in various embodiments, the gripping arm 114 of the handle 110 may be biased so as to grip the plunger shaft 60 when the plunger shaft 60 is located between at least a portion of the gripping arm 114 and at least a portion of the handle mating portion 112. By gripping the plunger shaft 60 between at least a portion of the gripping arm 114 and at least a portion of the handle mating portion 112, the handle 110 may be prevented from disconnecting from the plunger shaft 60 until the handle 110 is rotated to a position where the plunger shaft 60 is not between the gripping arm 114 and the handle mating portion 112.

Figure 14:
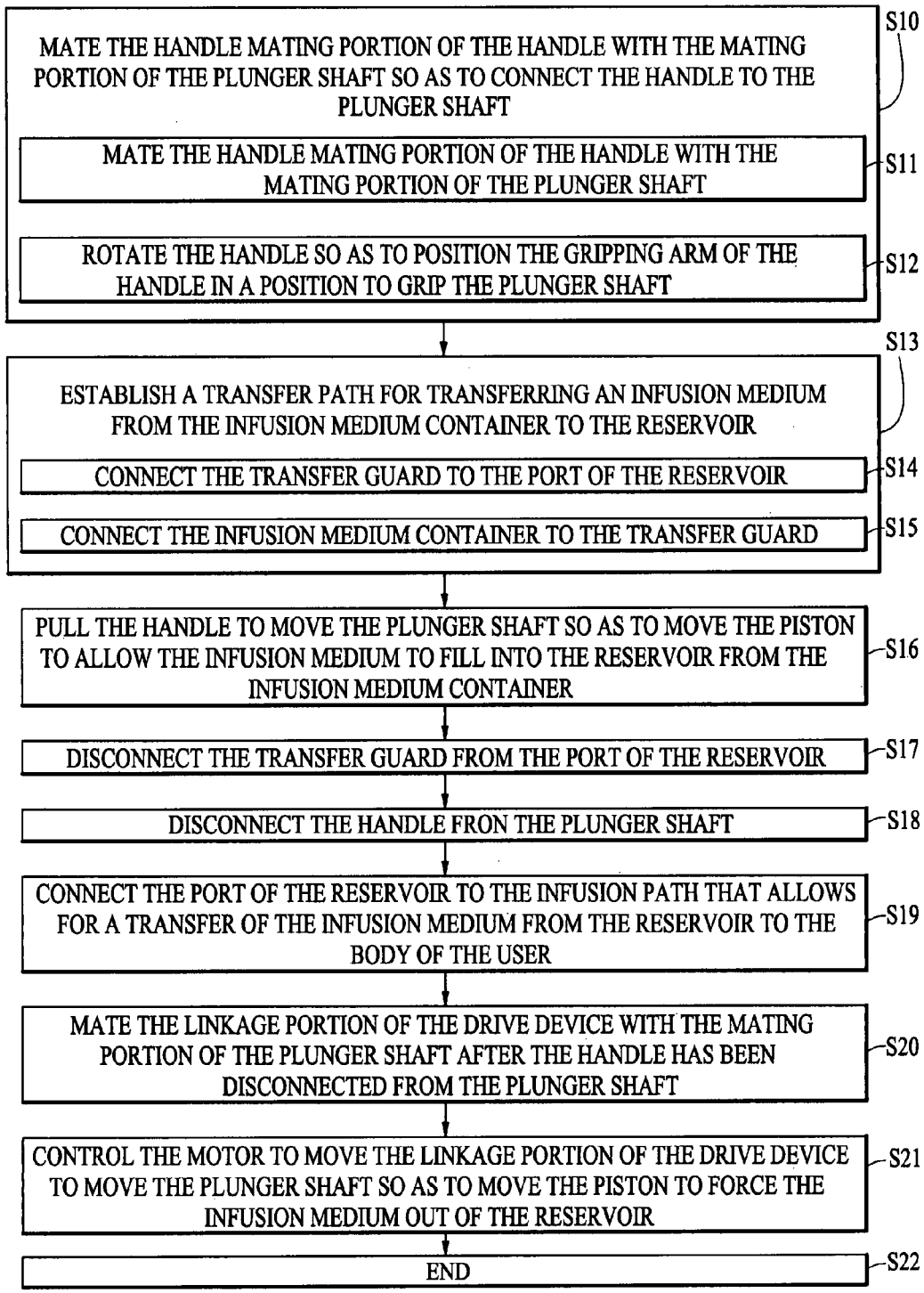
FIG. 14 illustrates a flow chart of a method of using an embodiment of a system in accordance with an embodiment of the present invention.

FIG. 14 illustrates a flow chart of a method of using an embodiment of the system 100 in accordance with an embodiment of the present invention. In describing the embodiment of the method illustrated by the flow chart in FIG. 14, reference will be made to various elements of embodiments of the system 100 illustrated in FIGS. 7-13. In S10, the handle mating portion 112 of the handle 110 is mated with the plunger shaft mating portion 62 of the plunger shaft 60, so as to connect the handle 110 to the plunger shaft 60. In various embodiments, the step S10 includes the step S11 of mating the handle mating portion 112 of the handle 110 with the plunger shaft mating portion 62 of the plunger shaft 60, and the step S12 of rotating the handle 110 so as to position the gripping arm 114 of the handle 110 in a position to grip the plunger shaft 60. The method then continues to S13.

In S13, a transfer path for transferring an infusion medium from the infusion medium container 130 to the reservoir 40 is established. In various embodiments, the step S13 includes the step S14 of connecting the transfer guard 120 to the port 41 of the reservoir 40, and the step S15 of connecting the infusion medium container 130 to the transfer guard 120. In some embodiments, the steps S10 and S13 are reversed such that a transfer path is established between the infusion medium container 130 and the reservoir 40 before the handle mating portion 112 is mated with the plunger shaft mating portion 62. The method then continues to S16.

In S16, the handle 110 is pulled to move the plunger shaft 60 so as to move the piston 70 to allow the infusion medium to flow or fill into the reservoir 40 from the infusion medium container 130, and the method continues to S17. In S17, the transfer guard 120 is disconnected from the port 41 of the reservoir 40, and the method continues to S18. In S18, the handle 110 is disconnected from the plunger shaft 60. The method then continues to S119.

In S19, the port 41 of the reservoir 40 is connected to the infusion path 50 that allows for a transfer of the infusion medium from the reservoir 40 to the body of a user, and the method continues to S20. In S20, the drive device linkage portion 82 of the drive device 80 is mated with the plunger shaft mating portion 62 of the plunger shaft 60 after the handle 110 has been disconnected from the plunger shaft 60. The method then continues to S21. In S21, the motor 84 is controlled to move the drive device linkage portion 82 of the drive device 80 to move the plunger shaft 60 so as to move the piston 70 to force the infusion medium out of the reservoir 40. The method then ends in S22.

In accordance with the embodiment of the method of using the system 100 illustrated in FIG. 14, the reservoir 40 is able to be filled with an infusion medium from the infusion medium container 130. In various embodiments, the reservoir 40 is housed in the reservoir retaining portion 24 of the disposable housing 20 (refer to FIGS. 6A and 6B), and the reservoir retaining portion 24 has an opening such that the reservoir 40 is able to be filled with an infusion medium from the infusion medium container 130 while the reservoir 40 is located within the reservoir retaining portion 24 of the disposable housing 20.

In various embodiments, the reservoir 40 is able to be refilled with an infusion medium using the method illustrated in FIG. 14. Thus, in various embodiments, the system 100 allows for filling and/or refilling of the reservoir 40. In some embodiments, the reservoir 40 may be partially filled with the infusion medium, while in other embodiments, the reservoir 40 may be completely filled with the infusion medium. Also, in some embodiments, the reservoir 40 may have measurement marks printed on a surface of the reservoir 40 so that the reservoir 40 can be filled with a measured amount of an infusion medium. Moreover, in various embodiments, the handle 110 is able to be pushed when the handle mating portion 112 is mated with the plunger shaft mating portion 62 so as to advance the piston 10 within the reservoir 40.

Figure 15:
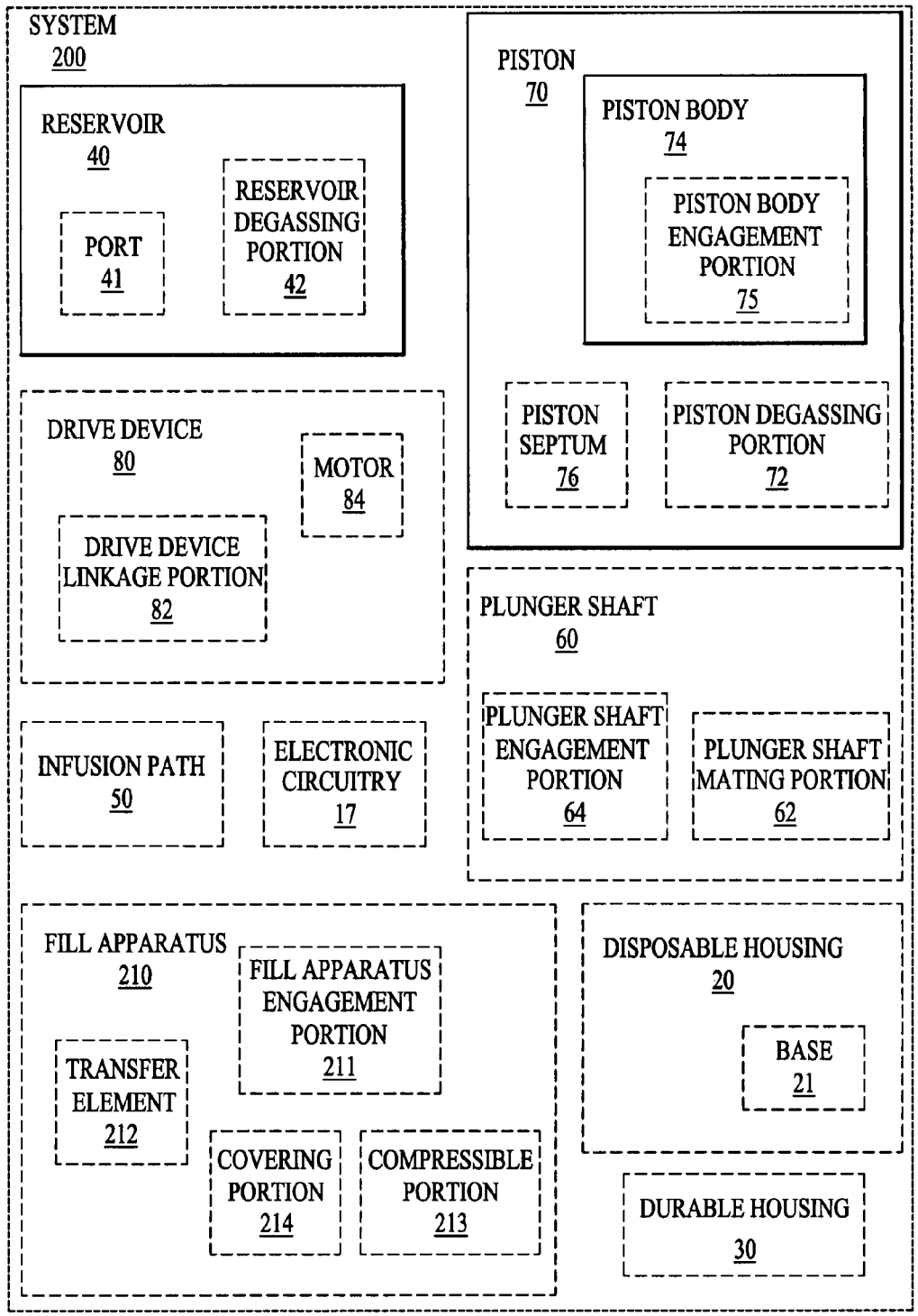
FIG. 15 illustrates a block diagram of a system in accordance with an embodiment of the present invention.

FIG. 15 illustrates a block diagram of a system 200 in accordance with an embodiment of the present invention. In various embodiments, the system 200 includes a reservoir filling system that allows for filling a reservoir, or the like. Also, in various embodiments, the system 200 includes a delivery device, such as the delivery device 12 (refer to FIGS. 2 and 3), or the like. In some embodiments, the system 200 includes an infusion medium delivery system, such as the infusion medium delivery system 10 (refer to FIG. 1), or the like. In various embodiments, the system 200 includes the reservoir 40 and the piston 70. Also, in various embodiments, the system 200 further includes the plunger shaft 60, the drive device 80, the infusion path 50, the disposable housing 20, the durable housing 30, the electronic circuitry 17, and a fill apparatus 210.

In various embodiments, the piston 70 includes a piston body 74 for forcing an infusion medium out of the reservoir 40. Also, in various embodiments, the piston body 74 is configured to have an opening. In some embodiment, the piston body 74 is configured to have an opening from a first surface of the piston body 74 that faces an infusion medium retaining interior volume 44 (refer to FIG. 8) of the reservoir 40 to a second surface of the piston body 74 that faces away from the infusion medium retaining interior volume 44 of the reservoir 40.

In various embodiments, the piston body 74 is configured to have an opening and the piston 70 further includes a piston septum 76 that is capable of being pierced to allow an infusion medium to be filled into or flow into the reservoir 40 through the opening in the piston body. In some embodiments, the piston septum 76 is located within an opening in the piston body 74. Also, in some embodiments, the piston septum 76 covers an opening in the piston body 74. In various embodiments, the piston septum 76 is formed of a suitable material such as, but not limited to, rubber, silicone rubber, polyurethane, or other materials that may be pierced by a needle and form a seal around the needle. Also, in various embodiments, the piston septum 76 is a self-sealing septum, such that the piston septum 76 closes so as to create a seal when the piston septum 76 is not being pierced.

Moreover, in various embodiments, the piston body 74 includes a piston body engagement portion 75 and the plunger shaft 60 includes a plunger shaft engagement portion 64, where the plunger shaft engagement portion 64 is able to be engaged with the piston body engagement portion 75. In various embodiments, the plunger shaft engagement portion 64 of the plunger shaft 60 includes a threaded screw or the like, and the piston body engagement portion 75 includes a threaded receptacle or the like for receiving the threaded screw of the plunger shaft engagement portion 64. Various other embodiments of the system 200 may have different structures for allowing for engagement of the piston body 74 with the plunger shaft 60, such as keyed structures, a tongue and groove structure, or the like.

In various embodiments of the system 200, the fill apparatus 210 includes a transfer element 212, such as a needle or the like, that is capable of piercing the piston septum 76. In further embodiments of the system 200, the fill apparatus 210 further includes a fill apparatus engagement portion 211, and the piston body 74 includes the piston body engagement portion 75, where the fill apparatus engagement portion 211 of the fill apparatus 210 is able to be engaged with the piston body engagement portion 75 of the piston body 74. In various embodiments, the fill apparatus engagement portion 211 includes a threaded portion, a keyed portion, a protrusion, a groove, or the like.

In various embodiments, the fill apparatus 210 further includes a covering portion 214 for at least partially surrounding a first end of the transfer element 212. Also, in various embodiments, the covering portion 214 is configured to be able to be placed over at least a portion of an infusion medium container, such as the infusion medium container 130 (refer to FIG. 10). In some embodiments, the fill apparatus 210 further includes a compressible portion 213 that is able to be compressed. In various embodiments, the compressible portion 213 includes a bellows or the like that is connected to the covering portion 214 and to the transfer element 212. Also, in various embodiments, the piston 70 includes the piston septum 76 and the piston body 74 with the piston body engagement portion 75, and the fill apparatus 210 is configured such that the transfer element 212 pierces the piston septum 76 when (i) the fill apparatus engagement portion 211 is engaged with the piston body engagement portion 75 and (ii) the compressible portion 213 of the fill apparatus 210 is compressed. In various embodiments, the fill apparatus 210 includes one or more of metal, plastic, rubber, glass, or the like.

Figure 16:
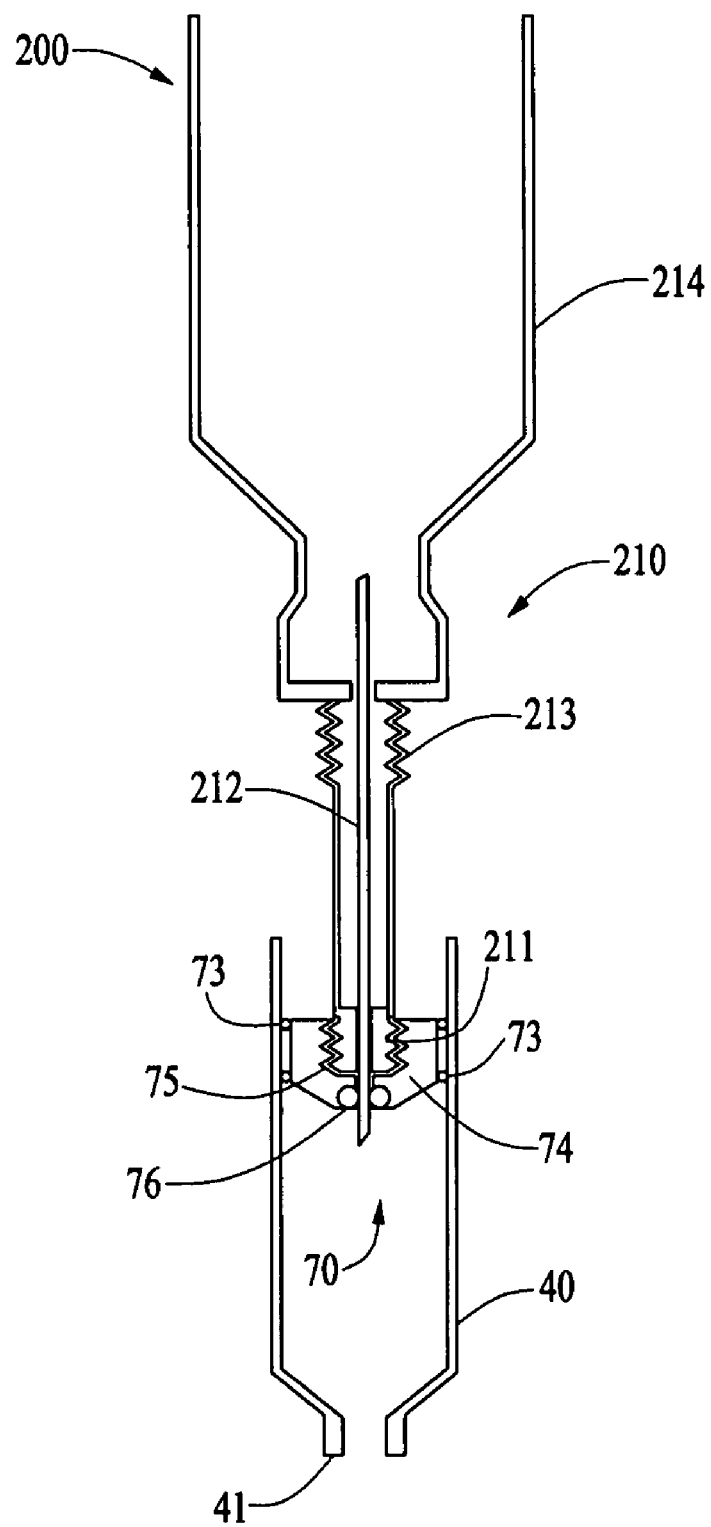
FIG. 16 illustrates a portion of an embodiment of a system in accordance with an embodiment of the present invention.

FIG. 16 illustrates a portion of an embodiment of the system 200 in accordance with an embodiment of the present invention. As is illustrated in FIG. 16, in various embodiments, the piston 70 includes the piston body 74 with an opening, and also includes the piston septum 76 located at least partially within the opening in the piston body 74. In the embodiment illustrated in FIG. 16, the piston body 74 includes the piston body engagement portion 75 and the fill apparatus 210 includes the fill apparatus engagement portion 211, where the fill apparatus engagement portion 211 is able to be engaged with the piston body engagement portion 75. Also, in the embodiment illustrated in FIG. 16, the piston body engagement portion 75 includes a threaded receptacle, and the fill apparatus engagement portion 211 includes a threaded portion that is able to be screwed into the threaded receptacle of the piston body engagement portion 75. Various other embodiments may employ, for example, keyed structures, tongue and groove structures, or the like, for allowing the fill apparatus 210 to engage with the piston body 74.

In various embodiments of the system 200, the system 200 includes the fill apparatus 210 with the covering portion 214 and the covering portion 214 is capable of fitting over a vial, such as a 10 ml insulin vial, or the like. Also, in various embodiments of the system 200, the piston 70 includes the piston septum 76, and the fill apparatus 210 includes the covering portion 214 and the compressible portion 213. In such embodiments, the fill apparatus may be configured so that once the covering portion 214 has covered an infusion medium container, such as a vial or the like, and a user pushes on the infusion medium container, the compressible portion 213 is compressed to cause the transfer element 212 to pierce the piston septum 76 and establish a transfer path to transfer an infusion medium from the infusion medium container to the reservoir 40.

In the embodiment of the system 200 illustrated in FIG. 16, once the covering portion 214 has been placed over an infusion medium container and the piston septum 76 has been pierced with the transfer element 212 of the fill apparatus 210, the transfer element 212 provides a transfer path for transferring an infusion medium from the infusion medium container to the reservoir 40 through an opening in the piston body 74. Then, the fill apparatus 210 and the reservoir 40 may be oriented such that the fill apparatus 210 is above the reservoir 40, and the fill apparatus 210 may be pulled to cause fluid to flow out of the infusion medium container and into the reservoir 40. In some alternate embodiments, the fill apparatus 210 and the reservoir 40 may be oriented such that the fill apparatus 210 is below the reservoir 40, and fluid may be drawn from the infusion medium container into the reservoir 40. In such alternate embodiments, the transfer element 212 may need to be longer than in embodiments where, for filling the reservoir 40, the reservoir 40 is oriented such that the fill apparatus 210 is above the reservoir 40. Thus, various embodiments of the system 200 allow for filling the reservoir 40 with an infusion medium through the piston body 74, which allows for filling the reservoir 40 without having to fill the reservoir 40 through the port 41.

Thus, various embodiments of the system 200 allow for an infusion path, such as the infusion path 50 (refer to FIG. 2), from the reservoir 40 to a user to be isolated from a filling process to fill the reservoir 40, because the reservoir 40 may be filled with an infusion medium through the opening in the piston body 74, which is a different opening than the port 41 of the reservoir 40 from which the infusion path may receive the infusion medium. Also, embodiments of the system 200 that use a needle for the transfer element 212 of the fill apparatus 210 allow for protecting a user from contact with the needle by providing the covering portion 214 and by providing the compressible portion 213 that expands when the fill apparatus 210 is not being compressed to cause the needle to be covered. Thus, various embodiments of the system 200 allow for making a filling process safer by protecting a user from contact with a needle used as the transfer element 212.

FIG. 17 illustrates another portion of an embodiment of the system 200 in accordance with an embodiment of the present invention. With comparison to FIG. 16, the embodiment of FIG. 17 illustrates that the fill apparatus 210 (refer to FIG. 16) is able to be disconnected from the piston body 74. In various embodiments, the system 200 includes the piston septum 76, and the piston septum 76 is self-sealing such that the piston septum 76 is able to seal after being pierced so as to keep an infusion medium within the reservoir 40 when the piston septum 76 is not being pierced. In various embodiments, the plunger shaft 60 includes the plunger shaft engagement portion 64 that is able to be engaged with the piston body engagement portion 75 so as to connect the plunger shaft 60 to the piston body 74.

FIG. 18 illustrates the portion of an embodiment of the system 200 in accordance with the embodiment illustrated in FIG. 17. As is illustrated in FIG. 18, in various embodiments, the piston body 74 includes a piston body engagement portion 75 and the plunger shaft 60 includes a plunger shaft engagement portion 64 that is able to be engaged with the piston body engagement portion 64. Also, in such embodiments, when the plunger shaft engagement portion 64 of the plunger shaft 60 is engaged with the piston body engagement portion 75 of the piston body 74, at least a portion of the plunger shaft mating portion 62 of the plunger shaft 60 may be exposed outside of the reservoir 40 so as to allow for mating with the drive device linkage portion 82 of the drive device 80 (refer to FIGS. 8 and 9).

Figure 19:
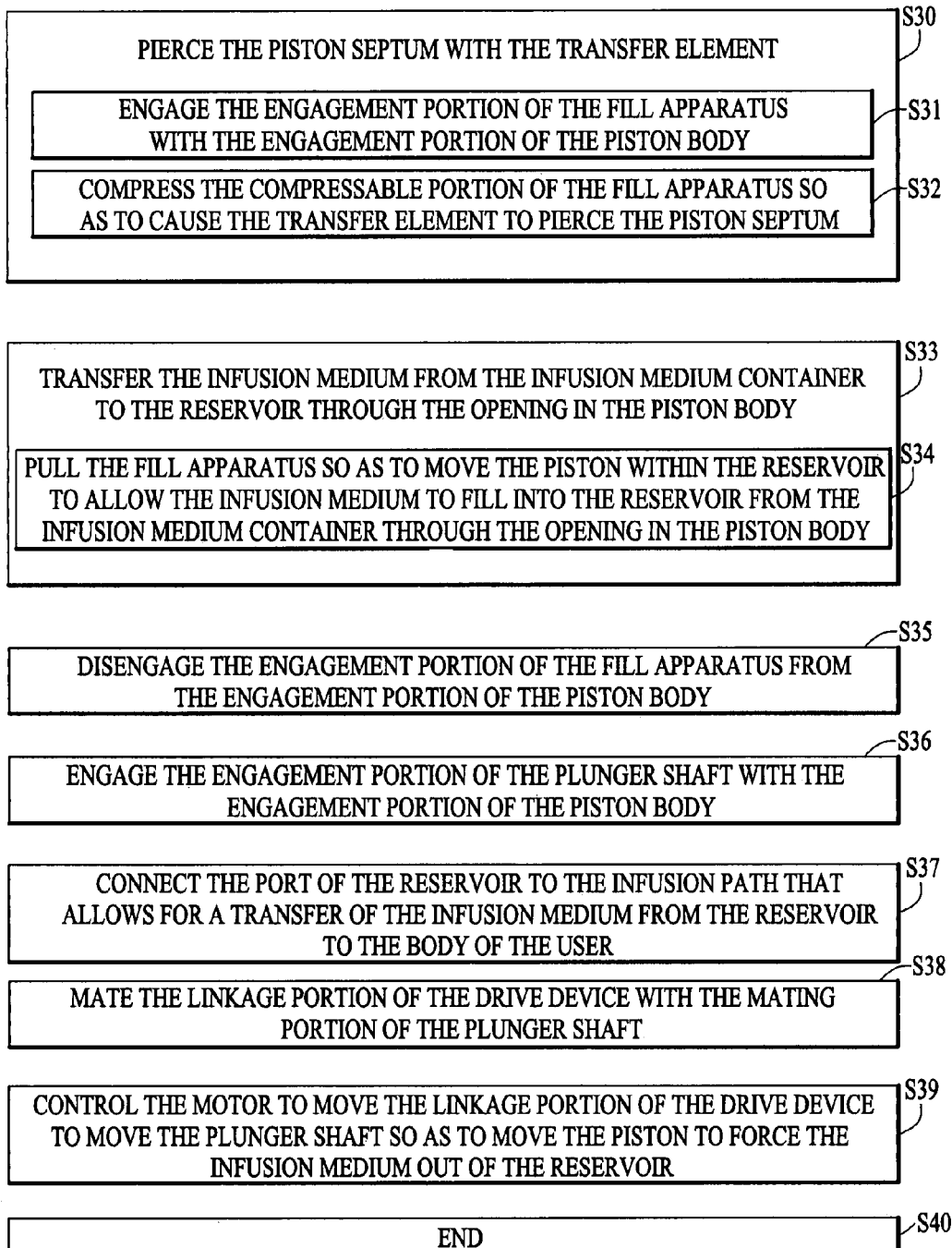
FIG. 19 illustrates a flow chart of a method of using an embodiment of a system in accordance with an embodiment of the present invention.

FIG. 19 illustrates a flow chart of a method of using an embodiment of the system 200 in accordance with an embodiment of the present invention. In describing the embodiment of the method illustrated by the flow chart in FIG. 19, reference will be made to various elements of embodiments of the system 200 illustrated in FIGS. 15-18. In S30, the piston septum 76 is pierced with the transfer element 212 of the fill apparatus 210. In various embodiments, the step S30 includes a step S31 of engaging the fill apparatus engagement portion 211 with the piston body engagement portion 75. Also, in various embodiments, the step S30 further includes a step S32 of compressing the compressible portion 213 of the fill apparatus 210 so as to cause the transfer element 212 to pierce the piston septum 76. The method then continues to S33.

In S33, an infusion medium is transferred from an infusion medium container to the reservoir 40 through an opening in the piston body 74. In some embodiments, the step S33 includes a step S34 of pulling the fill apparatus 210 so as to move the piston 70 within the reservoir 40 to allow the infusion medium to fill or flow into the reservoir 40 from the infusion medium container through the opening in the piston body 74. The method then continues to S35.

In S35, the fill apparatus engagement portion 211 of the fill apparatus 210 is disengaged from the piston body engagement portion 75, and the method continues to S36. In S36, the plunger shaft engagement portion 64 is engaged with the piston body engagement portion 75, and the method continues to S37. In S37, the port 41 of the reservoir 40 is connected to the infusion path 50 that allows for a transfer of the infusion medium from the reservoir 40 to the body of a user. The method then continues to S38.

In S38, the drive device linkage portion 82 of the drive device 80 is mated with the plunger shaft mating portion 62 of the plunger shaft 60, and the process continues to S39. In S39, the motor 84 is controlled to move the drive device linkage portion 82 of the drive device 80 to move the plunger shaft 60 so as to move the piston 70 to force the infusion medium out of the reservoir 40 and deliver the infusion medium to the body of the user. The method then ends at S40.

Figure 20:
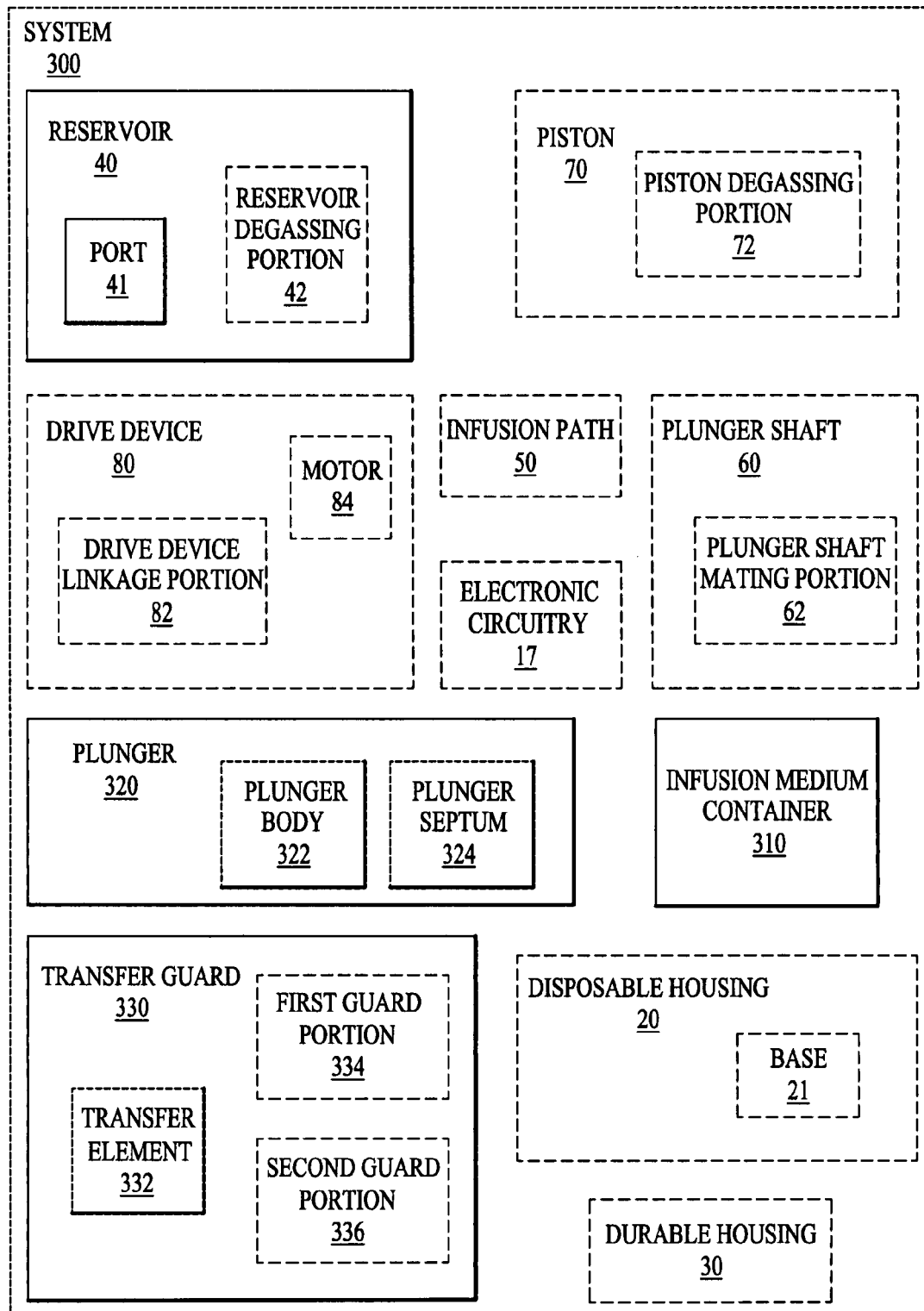
FIG. 20 illustrates a block diagram of a system in accordance with an embodiment of the present invention.

FIG. 20 illustrates a block diagram of a system 300 in accordance with an embodiment of the present invention. In various embodiments, the system 300 includes a reservoir filling system that allows for filling a reservoir, or the like. Also, in various embodiments, the system 300 includes a delivery device, such as the delivery device 12 (refer to FIGS. 2 and 3), or the like. In some embodiments, the system 300 includes an infusion medium delivery system, such as the infusion medium delivery system 10 (refer to FIG. 1), or the like. In various embodiments, the system 300 includes the reservoir 40, an infusion medium container 310, a plunger 320, and a transfer guard 330. Also, in various embodiments, the system 300 further includes the piston 70, the plunger shaft 60, the infusion path 50, the drive device 80, the electronic circuitry 17, the disposable housing 20, and the durable housing 30.

The infusion medium container 310 allows for holding an infusion medium. In various embodiments, the infusion medium container 310 includes a vial, a canister, or the like. The plunger 320 is disposed at least partially within the infusion medium container 310, and the plunger 320 is moveable within the infusion medium container 310. The plunger 320 includes a plunger body 322 and a plunger septum 324. The plunger body 322 is configured to allow for forcing the infusion medium out of the infusion medium container 310, and the plunger body 322 is configured to have an opening.

The plunger septum 324 is capable of being pierced to allow the infusion medium to flow out of the infusion medium container 310 through the opening in the plunger body 322. The plunger body 322 may be made of a suitably rigid material such as, but not limited to, metal, plastic, ceramic, glass, a composite material, or the like. The plunger septum 324 may be formed of a suitable material such as, but not limited to, rubber, silicone rubber, polyurethane, or other materials that may be pierced by a needle and form a seal around the needle. In various embodiments, the plunger septum 324 includes a self-sealing septum.

The transfer guard 330 includes a transfer element 332 for piercing the plunger septum 324 and for providing a path to allow the infusion medium to be transferred from the infusion medium container 310 to the reservoir 40. In various embodiments, the transfer element 332 includes a needle or the like. In some embodiments, the transfer guard 330 further includes a first guard portion 334 and a second guard portion 336. The first guard portion 334 is capable of at least partially surrounding a first end of the transfer element 332. The second guard portion 336 is capable of at least partially surrounding a second end of the transfer element 332. In various embodiments, the first guard portion 334 and the second guard portion 336 include one or more of metal, plastic, rubber, glass, composite material, or the like.

Figure 21:
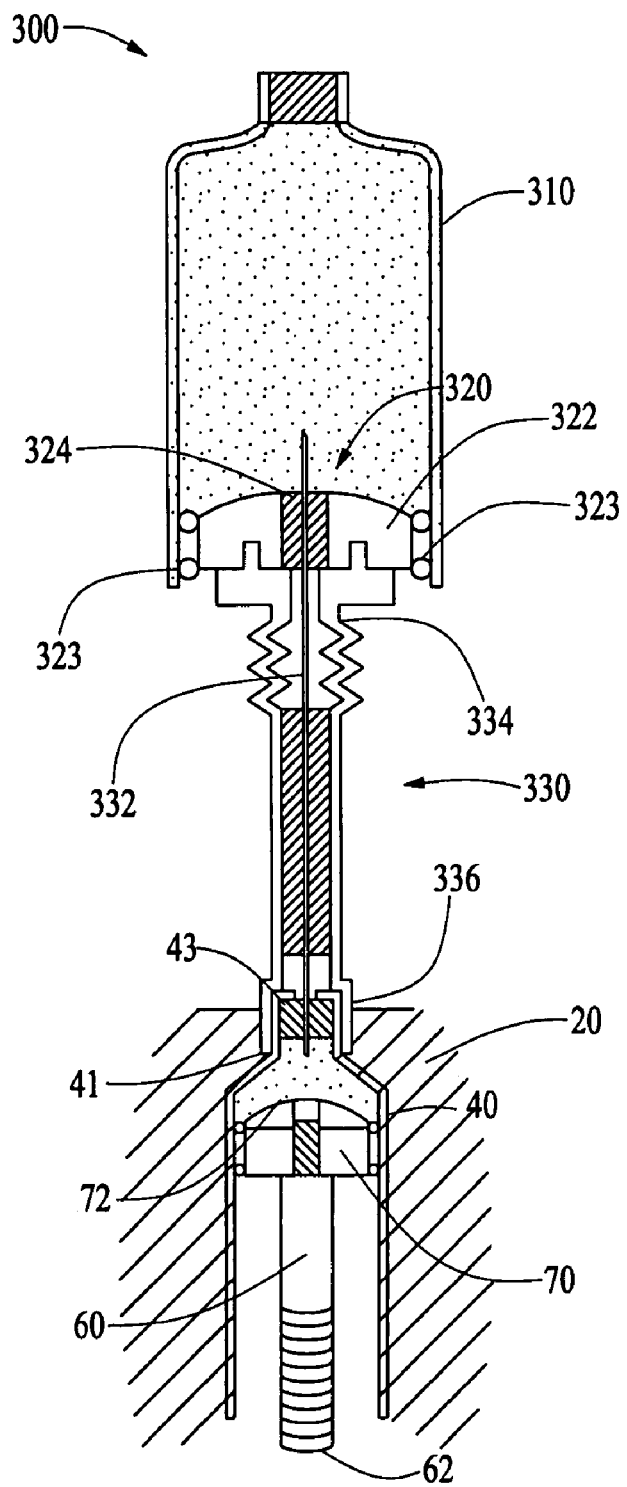
FIG. 21 illustrates a portion of an embodiment of a system in accordance with an embodiment of the present invention.

FIG. 21 illustrates a portion of an embodiment of the system 300 in accordance with an embodiment of the present invention. As is illustrated in FIG. 21, the infusion medium container 310 allows for holding an infusion medium, and the plunger 320 is disposed within the infusion medium container 310. The plunger 320 has the plunger body 322 with an opening, and the plunger septum 324 is located within the opening in the plunger body 322. In various embodiments, the plunger 320 has a diameter that is substantially the same as an inner diameter of the infusion medium container 310. Also, in various embodiments, the plunger 320 includes one or more seals 323, such as o-rings, for creating a seal between the plunger 320 and an inner surface of the infusion medium container 310. The plunger 320 is moveable within the infusion medium container 310.

In the embodiment of the system 300 illustrated in FIG. 21, the plunger septum 324 is capable of being pierced by one end of the transfer element 332 of the transfer guard 330. Also, another end of the transfer element 332 of the transfer guard 330 is able to pierce the septum 43 located in the port 41 of the reservoir 40. As a consequence, the transfer element 332 is able to provide a transfer path for transferring an infusion medium from the infusion medium container 310 to the reservoir 40. As is illustrated in FIG. 21, in various embodiments, the first guard portion 334 of the transfer guard 330 is able to be engaged with the plunger 320.

Also, in various embodiments, the first guard portion 334 includes a compressible portion, such as a bellows or the like, that expands to cover an end of the transfer element 332 when the transfer guard 330 is not engaged with the plunger 320, and that compresses to allow the end of the transfer element 332 to be exposed when the transfer guard 330 is engaged with the plunger 320. In some embodiments, the second guard portion 336 at least partially surrounds another end of the transfer element 332. Thus, in various embodiments, the transfer element 332 includes a needle and the transfer guard 330 is able to prevent the needle from being accessible unless the transfer guard 330 is engaged with the plunger 320 or the reservoir 40, so as to prevent injury to a user due to handling of the transfer guard 330.

In some embodiments, when the first guard portion 334 of the transfer guard 330 is mated with the plunger 320 and the second guard portion 336 of the transfer guard 330 is mated with the reservoir 40 such that the transfer element 332 provides the transfer path from the infusion medium container 310 to the reservoir 40, the plunger 320 is able to be advanced within the infusion medium container 310 so as to force an infusion medium from the infusion medium container 310 to the reservoir 40. In various embodiments, the plunger 320 is advanced within the infusion medium container 310 by, for example, a user pushing down on the infusion medium container 310. In some embodiments, the piston 70 with the attached or connected plunger shaft 60 is configured to be pushed back within the reservoir 40 as the infusion medium fills into the reservoir 40 through the port 41.

In various embodiments, the piston 70 includes the piston degassing portion 72 to allow for gases to be released from the reservoir 40 once the reservoir 40 has been filled with an infusion medium. In various embodiments, the piston degassing portion 72 includes a hydrophobic material that will allow air and other gases to pass through, but will substantially prevent the passage of an infusion medium, such as a liquid, syringe deliverable insulin, or the like. Examples of structures that permit air-flow, but that inhibit fluids can be found in U.S. patent application Ser. No. 10/328,393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety. In some embodiments, the system 300 includes the infusion path 50 and the infusion path 50 further includes a degassing portion (not shown in FIG. 21) for allowing gas to escape from the infusion path 50 while keeping the infusion medium within the infusion path 50.

In various embodiments that include the piston degassing portion 72, once gases are removed from the reservoir 40 through the piston degassing portion 72, the piston 70 is sealed to prevent gases from re-entering the reservoir 40 and to prevent evaporation of an infusion medium in the reservoir 40. In some embodiments that include the piston degassing portion 72, the piston degassing portion 72 is used to degas the reservoir 40 with positive pressure and then is removed or covered to prevent evaporation of an infusion medium that is in the reservoir 40.

In various embodiments, the system 300 includes the infusion path 50 and, once the reservoir 40 has been filled, the transfer guard 330 is removed or disconnected from the port 41 of the reservoir 40 and the infusion path 50 is connected to the port 41 of the reservoir 40. Thus, in various embodiments of the system 300, the reservoir 40 is able to be filled with an infusion medium from a same port that is used for delivering the infusion medium to the body of a user. In various other embodiments, the reservoir 40 includes a second port that is different from the port 41, and the second port is connected to the infusion path 50, such that the reservoir 40 is able to be filled with an infusion medium through a different port than a port that is used for delivering the infusion medium to the body of a user.

Figure 22:
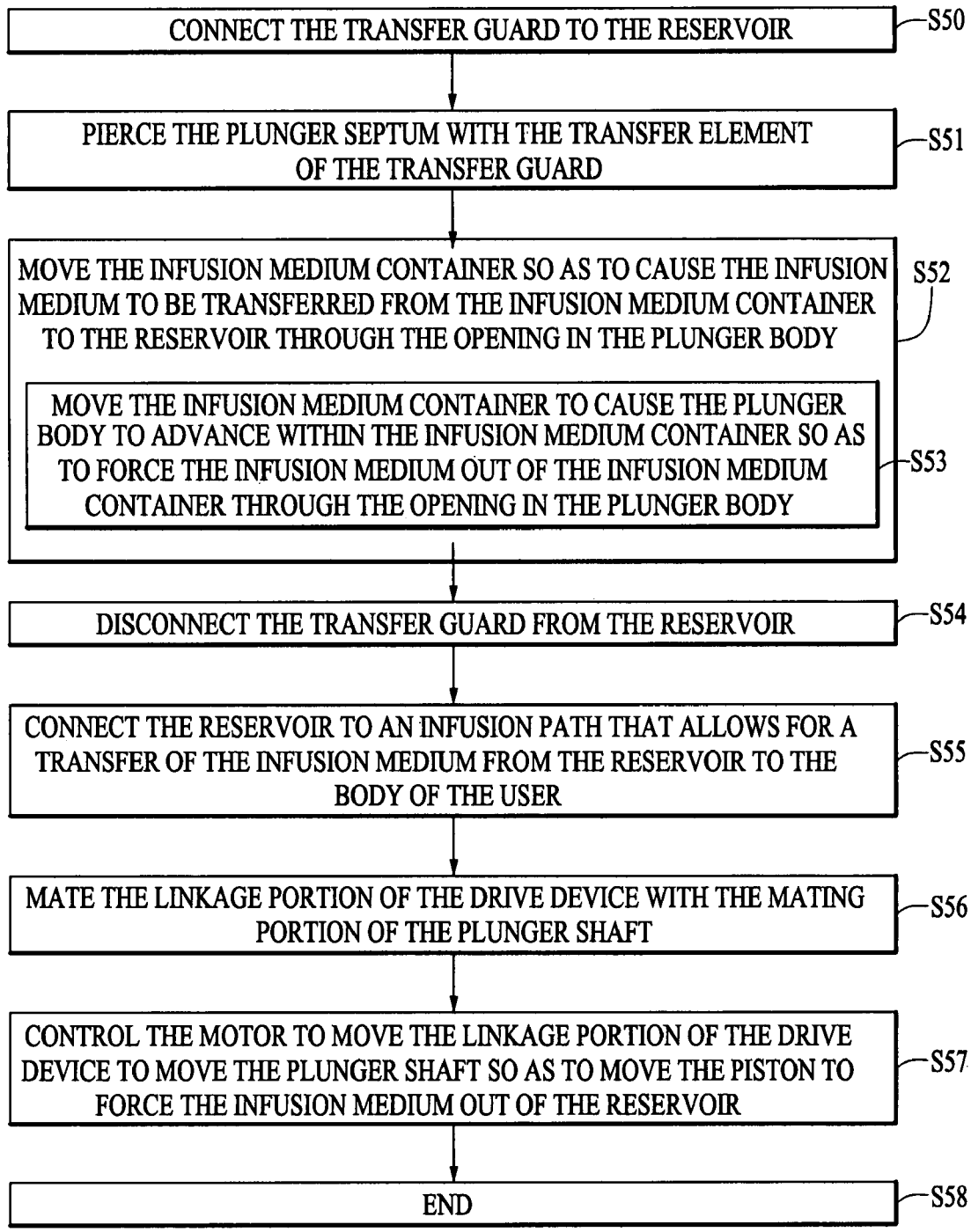
FIG. 22 illustrates a flow chart of a method of using an embodiment of a system in accordance with an embodiment of the present invention.

FIG. 22 illustrates a flow chart of a method of using an embodiment of the system 300 in accordance with an embodiment of the present invention. In describing the embodiment of the method illustrated by the flow chart in FIG. 22, reference will be made to various elements of embodiments of the system 300 illustrated in FIGS. 20-21. In S50, the transfer guard 330 is connected to the reservoir 40, and the method continues to S51. In S51, the plunger septum 324 of the plunger 320 is pierced with the transfer element 332 of the transfer guard 330, and the method continues to S52.

In S52, the infusion medium container 310 is moved so as to cause an infusion medium to be transferred from the infusion medium container 310 to the reservoir 40 through the opening in the plunger body 322. In various embodiments, the step S52 includes a step S53 of moving the infusion medium container 310 to cause the plunger body 322 to advance within the infusion medium container 310 so as to force the infusion medium out of the infusion medium container 310 through the opening in the plunger body 322. The method then continues to S54.

In S54, the transfer guard 330 is disconnected from the reservoir 40, and the method continues to S55. In S55, the reservoir 40 is connected to the infusion path 50 that allows for a transfer of the infusion medium from the reservoir 40 to the body of a user, and the method continues to S56. In S56, the drive device linkage portion 82 of the drive device 80 is mated with the plunger shaft mating portion 62 of the plunger shaft 60, and the method continues to S57. In S57, the motor 84 is controlled to move the drive device linkage portion 82 of the drive device 80 to move the plunger shaft 60 so as to move the piston 70 to force the infusion medium out of the reservoir 40 and into the body of the user. The method then ends at S58.

Figure 23:
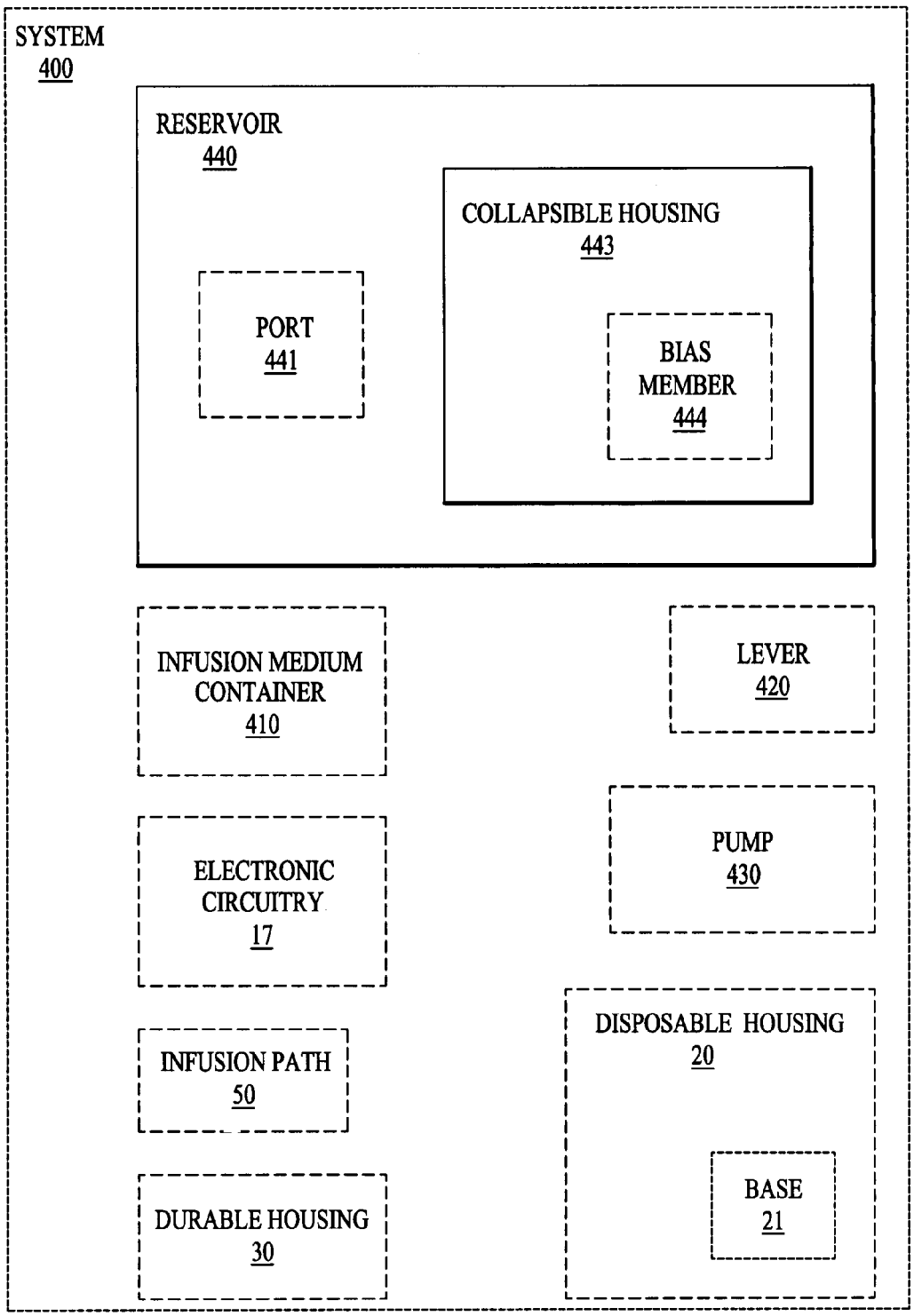
FIG. 23 illustrates a block diagram of a system in accordance with an embodiment of the present invention.

FIG. 23 illustrates a block diagram of a system 400 in accordance with an embodiment of the present invention. In various embodiments, the system 400 includes a reservoir filling system that allows for filling a reservoir, or the like. Also, in various embodiments, the system 400 includes a delivery device or the like. In some embodiments, the system 400 includes an infusion medium delivery system, such as the infusion medium delivery system 10 (refer to FIG. 1), or the like.

The system 400 includes a reservoir 440 for receiving an infusion medium from an infusion medium container 410. The reservoir 440 includes a collapsible housing 443 having an interior volume for holding the infusion medium, where the collapsible housing 443 is collapsible from an expanded state to reduce the interior volume and is expandable from a collapsed state to increase the interior volume, and the collapsible housing 443 is biased toward the expanded state. In various embodiments, the collapsible housing 443 includes a bellows or the like. Also, in various embodiments, the collapsible housing 443 includes metal, rubber, plastic, or the like. In some embodiments, the collapsible housing 443 includes at least one of titanium, stainless steel, or the like.

The collapsible housing 443 is configured such that upon the collapsible housing being expanded toward the expanded state, a pressure differential is created between the interior volume of the collapsible housing and the infusion medium container 410 sufficient to transfer the infusion medium from the infusion medium container 410 to the interior volume of the collapsible housing 443. In various embodiments, the collapsible housing 443 further includes a bias member 444 for biasing the collapsible housing 443 toward the expanded state. In various embodiments, the bias member 444 includes a spring, such as a coil spring, or the like. In some embodiments, the collapsible housing 443 may be configured as a structure that has its own spring force for biasing the collapsible housing 443 toward the expanded state.

In various embodiments, the system 400 further includes a lever 420. The lever 420 is moveable between a plurality of positions including a first position and a second position. The lever 420 is able to keep the collapsible housing 443 in the collapsed state when the collapsible housing 443 is in the collapsed state and the lever 420 is in the first position. In various embodiments, the collapsible housing 443 is able to expand to the expanded state when the lever 420 is in the second position. In some embodiments, the lever 420 is made of, for example, metal, plastic, rubber, glass, composite material, or the like. In some embodiments, the lever 420 is moveable among multiple positions along an expansion direction of the collapsible housing 443.

In various embodiments, the system 400 further includes a pump 430, such as a peristaltic pump or the like, for transferring an infusion medium from the collapsible housing 443 to the body of a user when the port 441 of the reservoir 440 is connected to the infusion path 50. In various embodiments, the pump 430 is a peristaltic pump or other pump that uses negative pressure to draw the infusion medium from the collapsible housing 443 and that is able to supply the infusion medium to the body of the user. In some embodiments, the system 400 further includes the disposable housing 20, the durable housing 30, and the electronic circuitry. In various embodiments, the disposable housing 20 includes the base 21 and the reservoir 440 is supported by the base 21. In some embodiments, the pump 430 is housed in the durable housing 30. Also, in some embodiments, the system 400 includes a screw driven slide (not shown) for causing an infusion medium to be transferred from the collapsible housing 443 to the body of a user when the port 441 of the reservoir 440 is connected to the infusion path 50.

FIG. 24 illustrates an embodiment of the system 400. In various embodiments, a formed metal bellows or the like is used as the collapsible housing 443. In some embodiments, the collapsible housing 443 includes a bellows and the bellows is configured with a built-in spring force that biases the bellows toward an expanded state. In FIG. 24, the collapsible housing 443 is illustrated as being in a collapsed state. In various embodiments, during assembly of the system 400, a vacuum device is applied to an interior of the bellows through a septum 447, such as a silicone septum or the like, in the port 441 so as to cause the collapsible housing 443 to collapse to the collapsed state.

FIG. 25 illustrates an embodiment of the system 400. As is illustrated in FIG. 25, in various embodiments the collapsible housing is able to be kept in a collapsed state by the lever 420 when the lever is in a first position. In the embodiment illustrated in FIG. 25, the lever 420 is in the first position and the collapsible housing is held in the collapsed state by the lever 420. In various embodiments, an inherent spring force of the collapsible housing 440 biases the collapsible housing toward the expanded state. In various other embodiments, the bias member 444 (refer to FIGS. 23 and 24) biases the collapsible housing toward the expanded state. In some embodiments, the reservoir 440 is located at least partially within the disposable housing 20.

FIG. 26 illustrates an embodiment of the system 400. In the embodiment illustrated in FIG. 26, the system 400 further includes the infusion medium container 410, such as a vial, a canister, or the like, that allows for holding an infusion medium. As is illustrated in FIG. 26, a transfer element 450, such as a needle or the like, may be used to pierce the septum 447 of the reservoir 440 and to provide a transfer path for an infusion medium from the infusion medium container 410 to an interior volume 445 of the collapsible housing 443.

Also, in FIG. 26, the lever 420 is illustrated as being in the second position, such that the collapsible housing has been allowed to expand to the expanded state. In various embodiments, upon moving the lever 420 from the first position to the second position, the collapsible housing 443 expands toward the expanded state due to the bias of the collapsible housing, and a pressure differential is created between the interior volume 445 of the collapsible housing 443 and the infusion medium container 410 sufficient to transfer the infusion medium from the infusion medium container to the interior volume 445 of the collapsible housing 443. In various embodiments, the lever 420 is moveable among a plurality of positions. For example, in some embodiments, the lever 420 is movable among a plurality of positions along an expansion direction of the collapsible housing 443. Also, in various embodiments, the lever 420 is rotatable among a plurality of positions. In some embodiments, the lever 420 is moveable among a plurality of positions such that each position for the lever 420 allows for a different amount of expansion of the collapsible housing 443.

In various embodiments of the system 400, once the interior volume 445 of the collapsible housing 443 has been filled with an infusion medium, the transfer element 450 may be disconnected from the port 441 of the reservoir 440, and the port 441 of the reservoir 440 may be connected to the infusion path 50 to allow for transferring the infusion medium from the reservoir 440 to the body of a user. In some embodiments, the collapsible housing 443 is able to be pushed so as to collapse the collapsible housing 443 and force the infusion medium out of the collapsible housing 443. In some embodiments, the pump 430 is provided to draw the infusion medium out of the collapsible housing 443 through the port 441.

Figure 27:
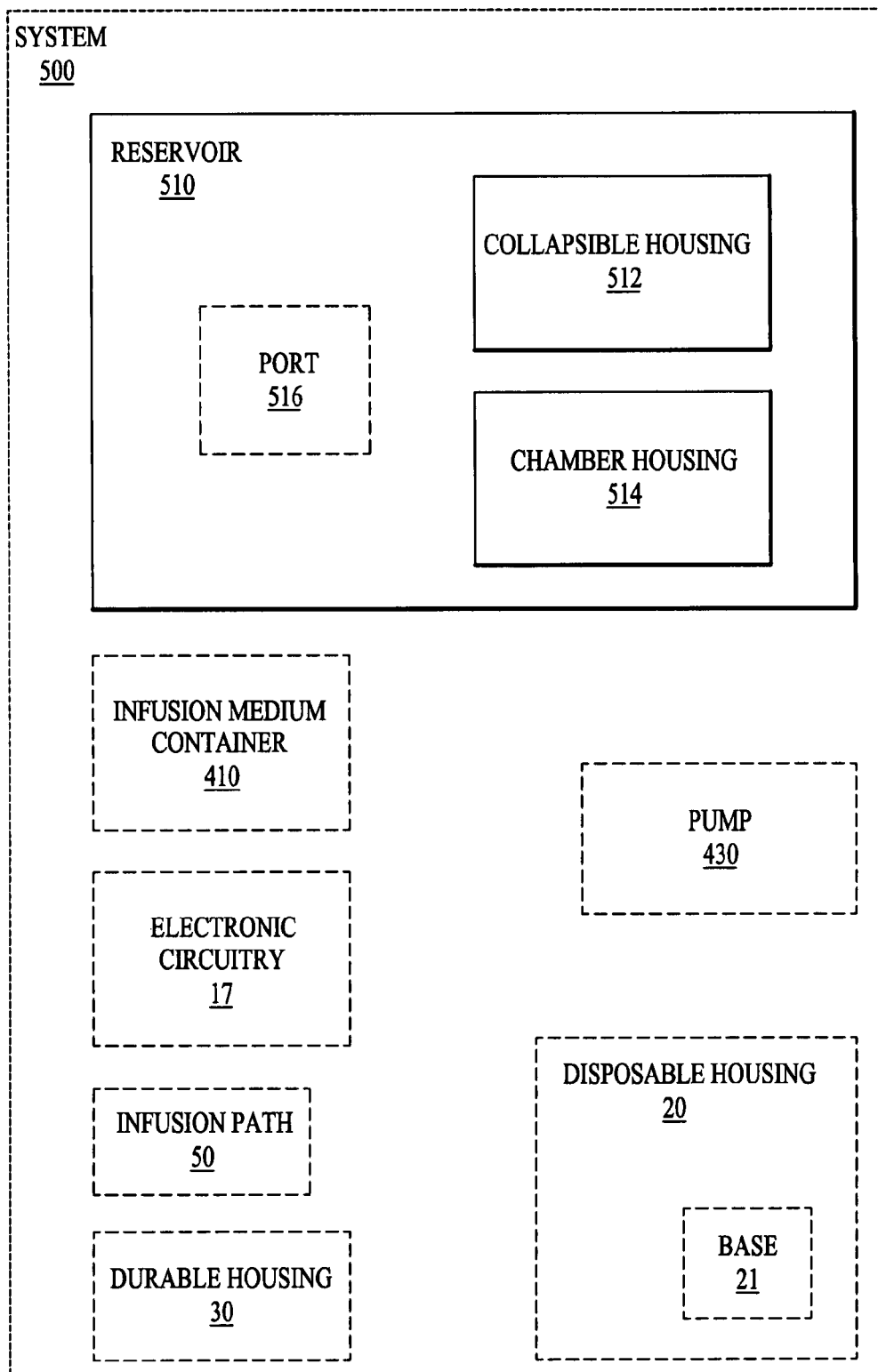
FIG. 27 illustrates a block diagram of a system in accordance with an embodiment of the present invention.

FIG. 27 illustrates a block diagram of a system 500 in accordance with an embodiment of the present invention. In various embodiments, the system 500 includes a reservoir filling system that allows for filling a reservoir, or the like. Also, in various embodiments, the system 500 includes a delivery device or the like. In some embodiments, the system 500 includes an infusion medium delivery system, such as the infusion medium delivery system 10 (refer to FIG. 1), or the like.

The system 500 includes a reservoir 510 for receiving an infusion medium from the infusion medium container 410. The infusion medium container has an interior volume for holding the infusion medium. The reservoir 510 includes a collapsible housing 512 and a chamber housing 514. The collapsible housing 512 has an interior volume for holding the infusion medium, where the collapsible housing 512 is collapsible from an expanded state to reduce the interior volume of the collapsible housing 512 and is expandable from a collapsed state to increase the interior volume of the collapsible housing 512. The chamber housing 514 has an interior volume bordered on at least one side by the collapsible housing 512 such that the interior volume of the chamber housing 514 increases as the collapsible housing 512 collapses toward the collapsed state and such that the interior volume of the chamber housing 514 decreases as the collapsible housing 512 expands toward the expanded state.

The collapsible housing 512 and the chamber housing 514 are configured such that when (i) a gaseous pressure within the interior volume of the chamber housing 514 is less than a particular gaseous pressure within the interior volume of the infusion medium container 410 and (ii) the collapsible housing 512 is in the collapsed state and (iii) a path for transferring the infusion medium is established between the interior volume of the infusion medium container 410 and the interior volume of the collapsible housing 512, the collapsible housing 512 and the chamber housing 514 allow for a pressure differential between the interior volume of the chamber housing 514 and the interior volume of the infusion medium container 410 to cause the collapsible housing 512 to expand and to cause the infusion medium to be pushed from the infusion medium container 410 to the collapsible housing 512.

In various embodiments, the collapsible housing includes a bellows or the like. Also, in various embodiments, the collapsible housing includes plastic or the like. In some embodiments, the collapsible housing includes one or more of metal, plastic, rubber, composite material, or the like. Also, in some embodiments, the system 500 further includes the disposable housing 20 and the durable housing 30, and the reservoir 510 is supported by the disposable housing 20. In some embodiments, the system 500 includes a screw driven slide (not shown) for causing an infusion medium to be transferred from the collapsible housing 512 to a body of a user.

Figure 28:
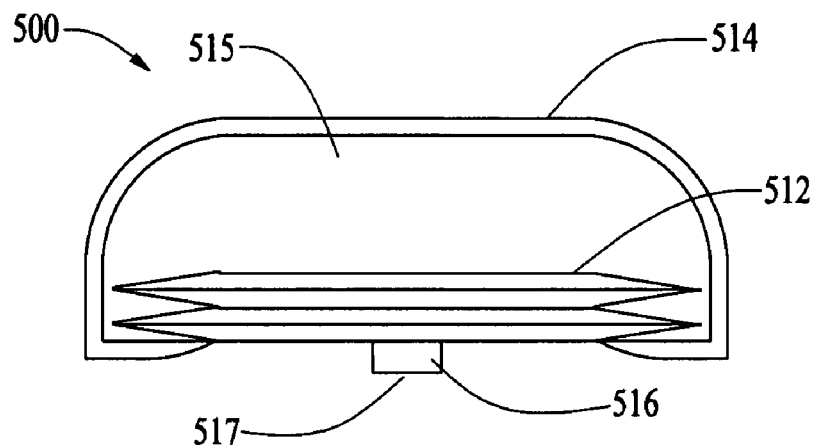
FIG. 28 illustrates an embodiment of a system in accordance with an embodiment of the present invention.

FIG. 28 illustrates an embodiment of the system 500. In FIG. 28, the collapsible housing 512 is shown in the collapsed state. An interior volume 515 of the chamber housing 514 is defined within the chamber housing 514, where the chamber housing is bordered on at least one side by the collapsible housing 512. A port 516 of the reservoir 510 is provided in various embodiments to allow for an infusion medium to flow into the collapsible housing 512 and to flow out of the collapsible housing 512. Also, in various embodiments, a pierceable septum, such as a self-sealing septum or the like, is provided within the port 516 to block the port 516 when the septum 517 is not pierced.

Figure 29:
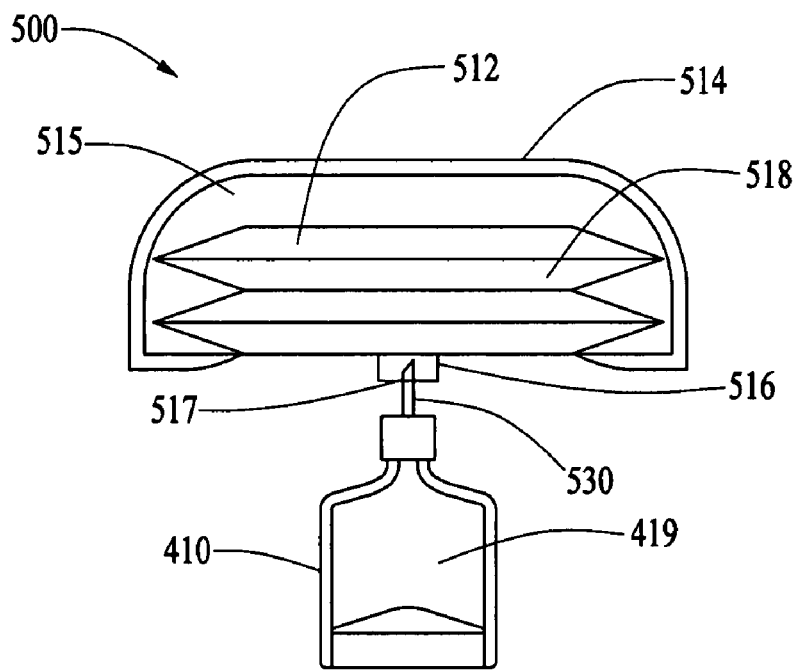
FIG. 29 illustrates an embodiment of a system in accordance with an embodiment of the present invention.

FIG. 29 illustrates an embodiment of the system 500. In FIG. 29, the collapsible housing 512 is shown in the expanded state. The interior volume 515 of the chamber housing 514 is reduced when the collapsible housing 512 expands from the collapsed state to the expanded state. Also, an interior volume 518 of the collapsible housing 512 increases as the collapsible housing 512 expands from the collapsed state to the expanded state. In the embodiment illustrated in FIG. 29, the system 500 further includes the infusion medium container 410 having an interior volume 419 for holding an infusion medium. In some embodiments, the system 500 further includes a transfer element 530, such as a needle or the like, that is able to pierce the septum 517 located within the port 516 of the reservoir 510.

In various embodiments, during assembly of the system 500, a vacuum is applied to the interior volume 515 of the chamber housing 514, causing the collapsible housing 512 to expand toward the expanded state. In some embodiments, the chamber housing 514 may be hermetically sealed. Then, during an assembly process in accordance with an embodiment of the present invention, a vacuum may be applied to the interior volume 518 of the collapsible housing 512 through the septum 517 to cause the collapsible housing 512 to collapse to the collapsed state.

After the system 500 has been assembled, in various embodiments, the collapsible housing 512 is able to be filled with an infusion medium by attaching the infusion medium container 410 to the transfer element 530 and then piercing the septum 517 of the reservoir 510 with the transfer element 530. Then, in some embodiments, a differential pressure between the vacuum of the interior volume 515 of the chamber housing 514 and the gaseous pressure of the interior volume 419 of the infusion medium container 410 causes the infusion medium to be transferred from the infusion medium container 410 to the reservoir 510.

In various embodiments, the port 516 of the reservoir 510 may be connected to the infusion path 50 to allow for delivering an infusion medium from the reservoir 510 to the body of a user. In some embodiments, the system 500 further includes the pump 430, such as a peristaltic pump or the like, for drawing the infusion medium out of the reservoir 510 and for delivering the infusion medium to the body of the user through the infusion path 50. In various embodiments, the system 500 further includes the electronic circuitry 17 for controlling the pump 430. Also, in various embodiments, system 500 includes the disposable housing 20, the durable housing 30, the reservoir 510, and the pump 430, where the reservoir 510 is supported by the disposable housing 20, and the pump 430 is housed in the durable housing 30. In some embodiments, the disposable housing 20 and the durable housing 30 may both be connected to a base element (not shown) that is then secured to a body of a user.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

What is claimed is:

1. A system, comprising:
   an infusion medium container for holding an infusion medium;
   a plunger disposed at least partially within the infusion medium container, the plunger being moveable within the infusion medium container, the plunger comprising:
      a plunger body for forcing the infusion medium out of the infusion medium container; and
      a plunger septum; and
   a transfer guard having a transfer element for piercing the plunger septum and for providing a path between the infusion medium container and a reservoir container to allow the infusion medium to be transferred from the infusion medium container to the reservoir container, the transfer guard configured to be attachable to and detachable from the reservoir container to allow removal of the reservoir container from the system.

2. The system of claim 1,
   wherein the infusion medium container comprises a vial.

3. The system of claim 1,
   wherein the transfer element comprises a needle.

4. The system of claim 3,
   wherein the transfer guard has a first guard portion for at least partially surrounding a first end of the needle; and
   wherein the transfer guard has a second guard portion for of at least partially surrounding a second end of the needle.

5. The system of claim 1,
   wherein the plunger septum is a self sealing septum that is able to seal after being pierced.

6. The system of claim 1, further comprising:
   a reservoir container for holding fluidic media, of the reservoir container having a port connectable to an infusion path to allow for delivering the infusion medium contained in the reservoir container to a body of a user upon being detached from the system.

7. The system of claim 1, further comprising:
   a reservoir container for holding fluidic media, wherein the reservoir container has a degassing portion that comprises a hydrophobic material for allowing gases to escape from the reservoir while keeping the infusion medium within the reservoir.

8. The system of claim 1, further comprising:
   a reservoir container for holding fluidic media; and
   a piston disposed at least partially within the reservoir container, the piston being moveable to allow the infusion medium to fill into the reservoir container from the infusion medium container and to force the infusion medium out of the reservoir container.

9. The system of claim 8,
   wherein the piston has a degassing portion that comprises a hydrophobic material for allowing gases to escape from the reservoir container while keeping the infusion medium within the reservoir container.

10. The system of claim 8, further comprising:
    a plunger shaft connected to the piston, the plunger shaft having a mating portion for mating with a linkage portion of a drive device, the drive device allowing for driving the plunger shaft so as to move the piston to force the infusion medium out of the reservoir container in a case where the linkage portion of the drive device is mated with the mating portion of the plunger shaft and the drive device drives the plunger shaft to move the piston.

11. The system of claim 10, further comprising:
    the drive device having the linkage portion;
    wherein the drive device further comprises a motor for moving the linkage portion.

12. The system of claim 11, further comprising:
    a disposable housing for housing the reservoir container; and
    a durable housing for housing the motor of the drive device, the durable housing configured to be selectively engaged with and disengaged from the disposable housing.

13. The system of claim 12,
    wherein the disposable housing is securable to a user.

14. The system of claim 12,
    wherein the durable housing is securable to a user.

15. The system of claim 12,
    wherein the disposable housing is securable to a user; and
    wherein the durable housing is securable to the user.

16. A method for using a system, the system comprising an infusion medium container for holding an infusion medium, a plunger that is disposed at least partially within the infusion medium container, and a transfer guard, the plunger having a plunger body and a plunger septum, the plunger body for forcing the infusion medium out of the infusion medium container, the plunger septum capable of being pierced to allow the infusion medium to flow through the plunger body, the transfer guard having a transfer element the transfer guard configured to be attachable to and detachable from a reservoir container to allow removal of the reservoir container from the system, the method comprising:
    piercing the plunger septum with the transfer element of the transfer guard to provide a path between the infusion medium container and the reservoir container; and
    moving the infusion medium container relative to the reservoir container to cause the infusion medium to be transferred from the infusion medium container to the reservoir container through the plunger body.

17. The method of claim 16,
wherein
moving the infusion medium container relative to the reservoir container comprises:
moving the infusion medium container relative to the reservoir container to cause the plunger body to advance within the infusion medium container to force the infusion medium out of the infusion medium container through the plunger body.

18. The method of claim 16,
wherein piercing the plunger septum comprises:
piercing the plunger septum with the transfer element of the transfer guard to provide a path between the infusion medium container and the reservoir container; and
connecting the transfer guard to the reservoir container.

19. The method of claim 18,
wherein moving the infusion medium container relative to the reservoir container comprises:
moving the infusion medium container relative to the reservoir container to cause the infusion medium to be transferred from the infusion medium container to the reservoir container through the plunger body and through a port of the reservoir container; and
wherein the method further comprises:
disconnecting the transfer guard from the reservoir container to remove the reservoir from the system; and
connecting the port of the reservoir container to an infusion path that allows for a transfer of the infusion medium contained in the reservoir container to a body of a user.

20. The system of claim 1, the plunger body configured to have an opening for containing the plunger septum.

21. The system of claim 1, the plunger septum comprising a first material and the plunger body comprising a second material different from the first material.

22. The system of claim 1, the transfer guard having an end for engaging and disengaging a connector portion of the reservoir plunger in at least one of a friction-fit and snap-fit engagement and disengagement.

23. The system of claim 1, further comprising:
a reservoir container for holding fluidic media, the reservoir container having a wall defining an interior volume for receiving the infusion medium from the infusion medium container;
the transfer guard configured to be attachable to and detachable from the reservoir container to allow removal of the reservoir container including the wall from the system.

24. The system of claim 1, wherein the plunger is disposed within the infusion medium container in contact with the infusion medium contained in the infusion medium container.

25. A method of manufacturing a system, the method comprising:
providing an infusion medium container for holding an infusion medium;
disposing a plunger at least partially within the infusion medium container, the plunger being moveable within the infusion medium container, the plunger comprising:
a plunger body for forcing the infusion medium out of the infusion medium container; and
a plunger septum;
providing a transfer guard having a transfer element for piercing the plunger septum and for providing a path between the infusion medium container and a reservoir container to allow the infusion medium to be transferred from the infusion medium container to the reservoir container; and
configuring the transfer guard to be attachable to and detachable from the reservoir container to allow removal of the reservoir container from the system.

* * * * *